United States Patent
Haber et al.

(10) Patent No.: US 7,150,710 B2
(45) Date of Patent: Dec. 19, 2006

(54) THERAPEUTIC METHODS USING ELECTROMAGNETIC RADIATION

(75) Inventors: Constance Haber, Murrysville, PA (US); Allan Gardiner, Kensington, CA (US)

(73) Assignee: Photomed Technologies, Inc., Kensington, CA (US)

( * ) Notice: Subject to any disclaimer, the term of this patent is extended or adjusted under 35 U.S.C. 154(b) by 0 days.

(21) Appl. No.: 10/180,802

(22) Filed: Jun. 26, 2002

(65) Prior Publication Data

US 2003/0130709 A1 Jul. 10, 2003

Related U.S. Application Data

(60) Provisional application No. 60/301,319, filed on Jun. 26, 2001, provisional application No. 60/301,376, filed on Jun. 26, 2001.

(51) Int. Cl.
*A61N 2/00* (2006.01)

(52) U.S. Cl. .......................................... 600/9; 607/100

(58) Field of Classification Search ............. 600/9–15, 600/427, 474, 549, 557; 607/88–90, 100, 607/102, 108–111
See application file for complete search history.

(56) References Cited

U.S. PATENT DOCUMENTS

| | | | |
|---|---|---|---|
| 624,392 A | 5/1899 | Smith | |
| 1,525,541 A | 2/1925 | Hall | |
| 1,965,865 A | 7/1934 | Thompson | 128/23 |
| 2,227,422 A | 1/1941 | Boerstler | 128/397 |
| 3,437,803 A | 4/1969 | Seitz et al. | 240/1.4 |
| 3,930,149 A | 12/1975 | French | 240/41.15 |
| 4,101,957 A | 7/1978 | Chang | 362/268 |
| 4,240,133 A | 12/1980 | Haina et al. | 362/293 |
| 4,281,366 A | 7/1981 | Wurster et al. | 362/32 |
| 4,519,020 A | 5/1985 | Little | 362/268 |
| 4,535,394 A | 8/1985 | Dugre | 362/231 |
| 4,621,284 A | 11/1986 | Nishioka et al. | 358/98 |
| 4,745,531 A | 5/1988 | Leclercq | 362/281 |
| 4,930,504 A | 6/1990 | Diamantopoulos et al. | 128/395 |
| 4,989,604 A | 2/1991 | Fang | 128/421 |
| 5,001,556 A | 3/1991 | Nakamura et al. | 358/98 |
| 5,031,078 A | 7/1991 | Bornhorst | 362/32 |
| 5,265,598 A | 11/1993 | Searfoss et al. | 607/88 |
| 5,269,746 A | 12/1993 | Jacobson | 600/13 |
| 5,344,384 A | 9/1994 | Ostrow et al. | 600/13 |
| 5,358,503 A | 10/1994 | Bertwell et al. | 606/27 |
| 5,405,369 A | 4/1995 | Selman et al. | 607/88 |
| 5,441,531 A | 8/1995 | Zarate et al. | 607/90 |
| 5,616,140 A | 4/1997 | Prescott | 606/10 |
| 5,800,479 A | 9/1998 | Thiberg | 607/88 |
| 5,814,078 A | 9/1998 | Zhou et al. | 607/1 |
| 6,110,106 A | 8/2000 | MacKinnon et al. | 600/181 |
| 6,140,346 A | 10/2000 | Andrulis et al. | 514/323 |
| 6,157,854 A * | 12/2000 | Haber et al. | 600/427 |
| 6,238,425 B1 | 5/2001 | Thiberg | 607/88 |
| 6,302,900 B1 | 10/2001 | Riggs | 607/89 |
| 6,607,550 B1 | 8/2003 | Bertwell | 607/88 |

OTHER PUBLICATIONS

Alan B. Koshman, Dale H. Carnegie, and Thomas J. Burke. "Symptomatic Reversal of Peripheral Neuropathy in Patients with Diabetes," *Journal of the American Podiatric Medical Association*. vol. 92 No. 3, Mar. 2002.

Anders A.F. Sima, M.D., Ph.D. and Charles Laudadio, M.D. "Design of Controlled Clinical Trials for Diabetic Polyneuropathy," *Seminars in Neurology* vol. 16, No. 2, Jun. 1996.

Dr. DeSalvo, "Photonic Stimulator Therapy," Advanced Integrated Medical Center, Inc., http//desalvochiropractic.com/pdt.html, Sep. 20, 2000.

Green, et al. "Photon Stimulation: A New Form of Therapy for Chronic Diabetic Painful Neuropathy of the Feet." *Pain Digest*, 1999: 9:286-291.

* cited by examiner

*Primary Examiner*—John P. Lacyk
(74) *Attorney, Agent, or Firm*—Fliesler Meyer LLP

(57) ABSTRACT

This invention provides methods for treating a variety of disorders using electromagnetic radiation directed at excitable tissues, including nerves, muscles and blood vessels. By controlling the wavelength, the wavelength bandpass, pulse duration, intensity, pulse frequency, and/or variations of those characteristics over time, and by selecting sites of exposure to electromagnetic radiation, improvements in the function of different tissues and organs can be provided. By monitoring physiological variables such as muscle tone and activity, temperature gradients, surface electromyography, blood flow and others, the practitioner can optimize a therapeutic regimen suited for the individual patient.

33 Claims, 11 Drawing Sheets

Figure 2a
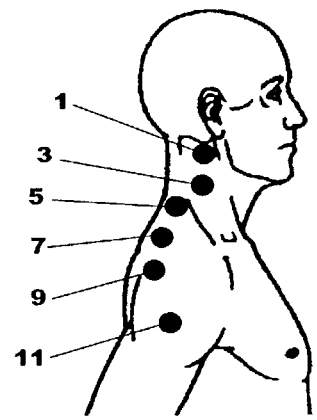
Figure 2b
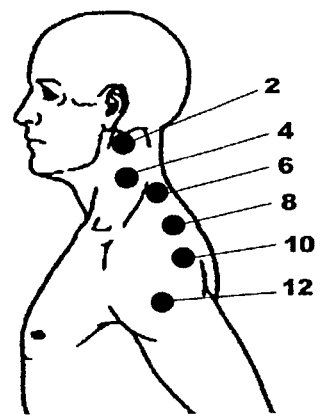
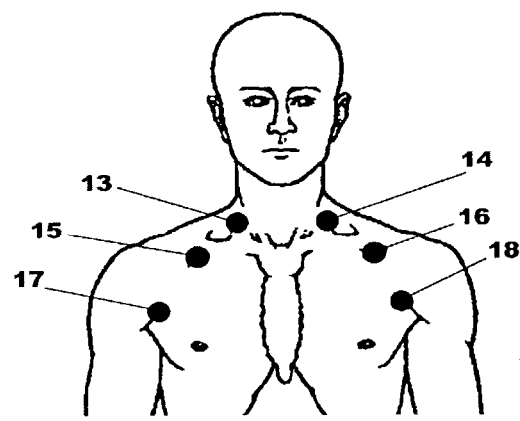
Figure 2c
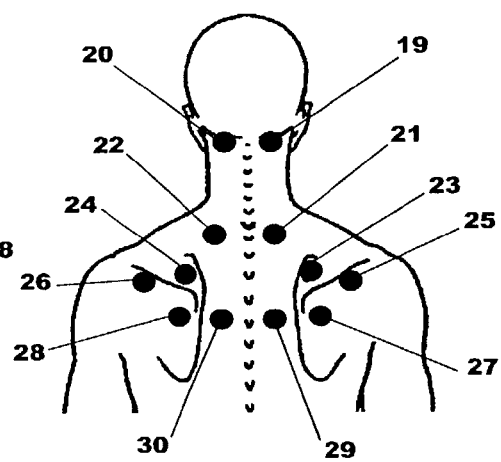
Figure 2d

THERAPEUTIC METHODS USING ELECTROMAGNETIC RADIATION

CLAIM OF PRIORITY AND RELATED APPLICATIONS

This U.S. Utility patent application claims priority to U.S. Provisional Patent Application, Ser. No. 60/301,319, entitled "Therapeutic Methods Using Electromagnetic Radiation," filed Jun. 26, 2001, and U.S. Provisional Patent Application Ser. No. 60/301,376, entitled "Multiple Wavelength Illuminator," filed Jun. 26, 2001.

This U.S. Utility patent application is related to U.S. Utility patent application Ser. No. 10/180,643, entitled "Multiple Wavelength Illuminator," Allan Gardiner and Constance Haber, inventors, filed Jun. 26, 2002, now U.S. Pat. No; 6,886,964, issued May 3, 2005 entitled: "illuminator with Filter Array and Bandwidth Controller." Each of the above applications and patent is expressly incorporated herein by reference as if seperately so incorporated.

BACKGROUND OF THE INVENTION

1. Field of the Invention

This invention relates to methods for treating pathophysiological conditions using electromagnetic radiation. More particularly, this invention relates to applying electromagnetic radiation having controlled wavelengths, bandwidths, pulse durations, pulse frequencies and/or intensities applied to areas of the body associated with a disorder to treat disorders of the musculature, nerves, blood vessels and other organs and tissues.

2. Related Art

Electromagnetic radiation is a subject of increasing focus by health care practitioners. Sunlight has been described to play an important role in health and the prevention of disease. A. Kime, M.D., *Sunlight;* World Health Publications, Pengrove, Calif., 1980 describes some health promoting benefits of exposure to sunlight. The electromagnetic spectrum relevant to health applications includes short wavelength ultraviolet ("UVA"), midrange and long wavelength ultraviolet ("UVB"), visible light, and infrared radiation. Ultraviolet light includes wavelengths of electromagnetic radiation of about 0.1 nanometer (nm) to about 380 nm. The ultraviolet spectrum can be considered to have several ranges. UVC has wavelengths in the range of about 0.1 nm to about 290 nm, UVA has wavelengths in the range of about 290 nm to about 320 nm, and UVB has wavelengths in the range of about 380 nm. Visible light is in the range of about 380 nm to about 780 nm, and infrared radiation has wavelengths in the range of about 780 nm to about 1000 micrometers ("μm").

Lasers and light emitting diodes have been used in acupuncture, pain management and tissue regeneration. Lasers produce coherent light, that is, having radiation waves that are in alignment with each other, and typically are of a single wavelength. In contrast, sunlight, light-emitting diodes (LEDs) and light from incandescent sources (e.g., filament light bulbs) produce non-coherent light, that is, radiation waves that are not in phase with each other. Moreover, non-coherent light typically comprises more than a single wavelength.

Ultraviolet light has been used to treat skin disorders and to promote the conversion of Vitamin D to Vitamin $D_3$, the active form of the vitamin. Flickering red lights have been used to treat premenstrual syndrome and migraine headaches. Other uses of flickering colored light include treatment of post-traumatic stress disorder. Additionally, skin cancer has been treated using a photochemically sensitive cream applied to the skin is taken up by cancer cells. Subsequent exposure to light having a wavelength of about 630 nm is then provided. The photochemical is activated within the cancer cells produce a toxic product that kills the cells.

Acupuncture is an ancient health care system based on twelve meridians on each side of the body and two master meridians along the center line of the body. Each meridian contains from about twenty-five (25) to about one-hundred fifty (150) acupuncture points. Many health problems are associated with abnormalities in the meridians. Acupuncture points are typically stimulated using needles inserted into the meridians, and also can be activated by electromagnetic radiation. Electromagnetic radiation has the advantages of being non-invasive, thus, not contributing to the spread of diseases including human immunodeficiency virus ("HIV"), hepatitis and other blood-borne disorders.

Infrared radiation and low energy lasers are used to treat a variety of different medical conditions. Photons can be delivered through the skin to underlying tissues, and can be absorbed by the tissue to activate structures without the potential for causing superficial damage to the skin. Stimulation of certain nerves by non-coherent electromagnetic radiation is associated with decreased pain (Haber et al., U.S. Pat. No. 6,157,854; PCT/US00/00911). U.S. Pat. No. 6,157,854 describes methods for simultaneously exposing acupuncture sites to localized infrared radiation and monitoring temperatures on a contralateral site on the body.

SUMMARY OF THE INVENTION

Thus, one object of this invention is the development of improved methods for treating disorders of the body using electromagnetic radiation.

Another object of this invention is the development of improved methods for evaluating the efficacy of therapy using electromagnetic radiation.

These and other objects are met by new methods for therapeutic application of electromagnetic radiation to tissues that are sensitive to such radiation. Therapeutic aims include normalization of blood flow to and from, and lymphatic flow from affected regions, and normalization of muscle tone, nerve activity and other tissue functions. Specific wavelengths can be chosen based on physiologic screening and sensitivity testing conducted prior to and during the application of treatment. Monitoring of patient's condition can be selected based on the patient's specific diagnosis and the organ systems and tissues affected.

Electromagnetic radiation therapy can be carried out by exposing a site on the body with localized non-coherent radiation of a desired peak wavelength and wavelength bandwidth (herein known as "bandwidth") which does not vary over time, including those in the infrared, visible, ultraviolet and other portions of the electromagnetic spectrum. Additionally, the wavelength used can vary over time. Fiber optics or other types of waveguides can direct beams of electromagnetic radiation to specific, pre-defined sites on a body with case. Additionally, with the advent of devices incorporating dual or multiple illumination systems (U.S. Provisional Patent Application titled: "Multiple Wavelength Illuminator", Allan Gardiner et al., inventors, filed Jun. 26, 2001, U.S. Utility patent application titled: "Multiple Wavelength Illuminator", Allan Gardiner et al., inventors, filed concurrently, each patent application incorporated herein fully by reference), it is now possible to provide, independently controlled beams of electromagnetic radiation to specific locations. In other aspects of this invention, a plurality of beams of electromagnetic radiation can be used either simultaneously or sequentially, and each having separately controllable wavelength, bandwidth, intensity, pulse duration, pulse frequency, phase or polarization.

In addition to providing a fixed, narrow bandpass beam, the wavelengths of electromagnetic radiation can be varied over time during application. For example, in some embodiments, it can be desirable to provide "wavelength variations" around a "central wavelength." In such embodiments, a central wavelength can be selected and the illuminator can be used to vary the wavelength to include wavelengths of longer or shorter wavelengths, typically in the range of about ±1 nm to about ±100 nm, alternatively about ±5 nm to about ±50 nm, in other embodiments in the range of about ±20 nm to about ±50 nm. It can be appreciated that other ranges of wavelength variation can be used. It can also be appreciated that one can have variations about a central wavelength that are asymmetrical, that is, the change in wavelength can be greater in one direction than in the other.

Similarly, the rate of change of wavelength, from the lowest to the highest can be in the range of about 1 sec to about 100 sec., alternatively about 5 sec to about 50 sec, in other embodiments in the range of about 20 sec to about 50 sec. Additionally, the rate of change of wavelength can be in the range of about 1 nm/sec to about 100 nm/sec, alternatively in the range of about 5 nm/sec to about 50 nm/sec, and in other embodiments, from about 20 nm/sec to about 50 nm/sec.

Moreover, the rate of change of wavelength can be varied, and includes by way of example only, linear changes over time, a sinusoidal output, whereby the rate of change of wavelength varies over time according to a sine wave function. In other embodiments, the change of wavelength can be trapezoidal. It can be appreciated that any type of a large number of variations in wavelength about a central wavelength can be used.

One or more of a number of methods for selecting and/or varying wavelength and/or wavelength variation over time can be used. For example, prisms, diffraction gratings, rulings, or filters can be relatively inexpensive. Alternatively, diode array emitters can be used.

A portion of a subject's body can be illuminated at locations designed to improve function. Trigger points, acupuncture points, electrodiagnostic points, nerve distributions or blood vessels can be illuminated singly or in combination. Additionally, to improve transparency of the subject's skin, a small drop of liquid can be used, such as water or oil.

Improved methods for evaluating effects of electromagnetic radiation therapy include, but are not limited to, the use of sensitive infrared cameras to monitor changes in body surface temperature ("thermography"), surface electromyography ("sEMG" or "SEMG"), oximetry, pulse volume, tissue compliance, monofilament testing, Doppler blood flow, pressure threshold, current perception threshold, electrodermal activity ("EDA"; a measurement of skin conductance), sweat tests such as the Alizarin Sweat Test, somatosensory testing, heart rate variability (including entrainment), nerve conduction velocity, campimetry, algorimetry, and other methods described herein below and those known in the diagnostic and/or evaluative arts.

To treat peripheral symptoms with electromagnetic therapy, it can be desirable to expose a nerve innvervating that site close to the exit of the nerve from the central nervous system (a "proximal" location). It can be desirable to expose a more peripheral part of the nerve (a "distal" location). Alternatively, it can be desirable to expose a nerve in an intermediate position between a distal site and a proximal site. Further, it can be desirable to simultaneously expose different locations of the same nerve to electromagnetic radiation, and in further embodiments, it can be desirable to expose nerves to radiation at different times in different locations.

To treat central nervous system disorders, it can be desirable to modify the activity of sensory afferent nerves. Alterations in sensory nerve activity can occur within structures in the spinal cord and/or the brain, including those structures that are responsible for pain transmission, motor function, or motor control.

Muscle cells and nerves to those muscles can be treated to cause relaxation, thereby decreasing muscle spasms and decreasing symptoms associated with muscle spasms, such as some types of headaches.

Electromagnetic radiation can be applied simultaneously to the eyes and/or ears or other sensory structures along with peripheral sites. By stimulating a central nervous system (CNS) site along with a peripheral site, providing "entrainment" or augmentation of therapeutic effects. Entrainment can be promoted by selecting pulse frequency and phase relationships between the CNS and peripheral stimuli. In addition to CNS sites, it can be desirable to stimulate a plurality of peripheral sites to entrain excitable tissues to produce enhanced therapeutic effects.

Although mechanisms underlying the therapeutic advantages of the methods of this invention are not precisely known, a possible mechanism may be that electromagnetic therapy can differentially stimulate or inhibit different types of excitable cells within a tissue to produce effects on those structures. Thus, according to this hypothesis, normalization of physiology of muscles, nerves, connective tissues and other tissues can be achieved by the application of specific electromagnetic radiation to tissues responsible for the abnormal function. Specific wavelength, bandwidth, wavelength variability over time, intensity, pulse duration, pulse frequency, polarization of the radiation, and duration of treatment by electromagnetic radiation can be selected by a physician or other practitioner based upon physiologic screening and by prior history.

BRIEF DESCRIPTION OF THE FIGURES

FIG. 1a depicts a situation in which a stimulator nerve and an inhibitory nerve act independently of one another to influence a third nerve.

FIG. 1b depicts a situation in which a stimulatory nerve inhibits the release of transmitter from an inhibitory nerve.

FIG. 1c depicts a situation in which an inhibitory nerve potentiates the release of transmitter from a stimulatory nerve.

FIG. 1d depicts a situation in which a stimulatory nerve potentiates the release of transmitter from an inhibitory nerve, and an inhibitory nerve inhibits the release of transmitter from a stimulatory nerve.

FIG. 1e depicts a situation in which stimulatory and inhibitory nerves inhibit transmitter release from the other.

FIG. 1f depicts a situation in which stimulatory and inhibitory nerves potentiate transmitter release from the other.

FIGS. 2a–2d each depict a view of a person's head and torso, indicating positions of selected sites of application of electromagnetic radiation useful in treating neuromuscular disorders according to this invention.

FIG. 3a depicts the SEMG trace of an affected side. FIG. 3b depicts the SEMG trace of a non-affected side of the patient. The numbers refer to onset of treatment using electromagnetic radiation in the visible range of the spectrum, and the + sign refers to cessation of illumination.

FIG. 4a depicts the SEMG trace of the affected side. FIG. 4b depicts the SEMG trace of the non-affected side.

FIG. 5a depicts the SEMG trace of the non-affected side. FIG. 5b depicts the SEMG trace of the affected side.

FIG. 6a depicts the SEMG trace of the non-affected side. FIG. 6b depicts the SEMG trace of the affected side.

DETAILED DESCRIPTION

Figure 1A:
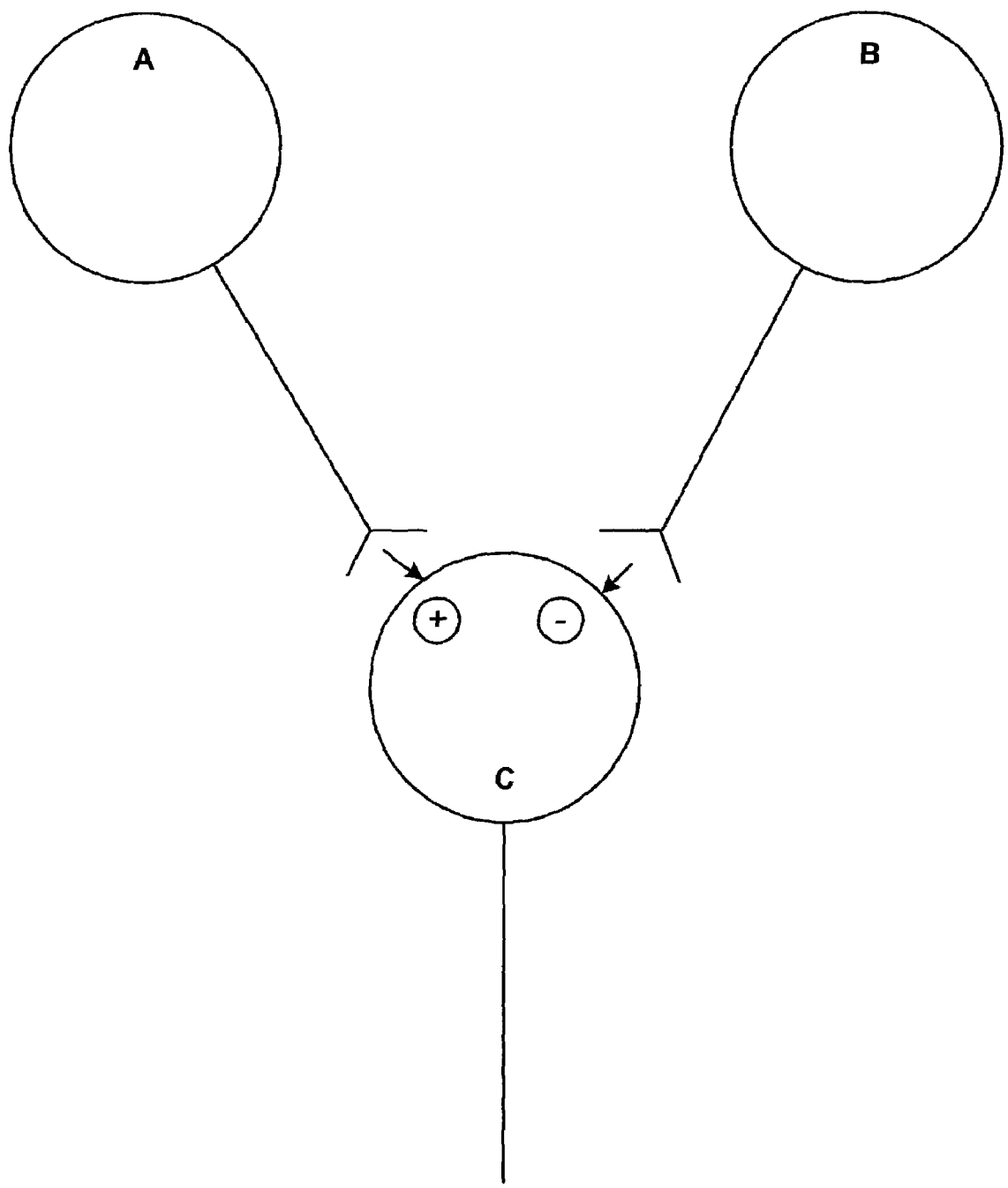
FIGS. 1a–1f depict schematic representations of some neural interactions.

This invention includes methods for treating a variety of physiological and pathophysiological conditions using electromagnetic radiation. Electromagnetic radiation can be delivered as a beam of radiation having defined wavelength, bandwidth, wavelength variability over time, intensity, pulse duration, pulse frequency, and/or polarization. Evaluation of therapeutic efficacy can be accomplished using several methods known in the art. It can be desirable to provide two or more separately controlled beams of electromagnetic radiation.

Numerous conditions can be treated using the methods of this invention. Muscular and connective tissue disorders include, by way of example only, sprains, strains, athletic injuries, spasms, fibromyalgia, trigger points, myofascial disorders, myalgia, myositis, overuse disorders, weakness from disuse, taut and tender fibers, chronic stress contractions, muscle spasm, lower extremity neuropathy and muscular rheumatism.

Nervous system disorders include, by way of example only, neuralgia, radiculalgia, radiculopathy, sciatica, carpal and tarsal syndromes, compressive neuropathies, autonomic nervous system disorders, post surgical pain syndrome, causalgia, RSD, complex regional pain syndrome, post herpetic pain syndrome, chronic pain syndrome, diabetic neuropathy and peripheral neuropathy.

Joint disorders include by way of example only, sprains, strains, degeneration, bursitis, tendonitis, subluxation, segmental dysfunction, articular disorder, postsurgical deformities and post fracture deformities. Disorders of the skin and integument include, by way of example only, lupus vulgaris, acne, eczema, psoriasis. Disorders of the ear, nose and throat include, by way of example only, tonsillitis, sore throat, gingivitis, thrush, and post nasal drip. Disorders of the genitourinary system includes, by way of example only, hemorrhoids, vulvodynia, pelvic floor ptosis, sphincter atony, urogenital pain and post-surgical pain. Disorders of the vascular system include, by way of example only, peripheral vascular insufficiency, Raynauds's syndrome, varix, and vasospasm.

I Selection of Therapeutic Variables

Electromagnetic radiation therapy can be applied using a range of therapeutic variables. Variables include the wavelength, bandwidth, the intensity, total radiation dose, pulse duration, pulse frequency, polarization of the radiation, and shape of the beam, among others. In certain embodiments, it can be desirable to use relatively narrow wavelengths of radiation in the visible spectrum, having a distinct "color." It can be desirable to vary the bandwidth of wavelengths used, resulting in therapy using a plurality of "colors". The descriptions of wavelengths are not limited, however, to visible light, but rather can be applied to any range of electromagnetic radiation having wavelengths in the ultraviolet, visible, infrared, or radio frequencies. Thus, in certain embodiments in which the optimum wavelength is not known, it can be desirable to apply a relatively broad spectrum of radiation around a certain wavelength. As therapy progresses, and the effects of therapy are monitored, one can progressively narrow or broaden the bandwidth of radiation as desired. Examples of devices for producing electromagnetic radiation having different bandwidths are described in U.S. Provisional Patent Application titled: "Multiple Wavelength Illuminator", Allan Gardiner et al., inventors, filed concurrently, and herein incorporated fully by reference. Although several applications described herein refer to filter-based illuminators, it is contemplated that other types of illuminators can be satisfactorily used.

The "bandwidth" of an illuminator is the range of wavelengths of radiation that are present in an output beam. For example, in a filter-based system, the bandwidth is the range of wavelengths that can pass through a filter or plurality of filters. A bandpass filter has a transmission that is high for a particular band of frequencies and with a lower transmission of frequencies above and below this band. The width or narrowness of the band for frequencies transmitted through a filter is often measured by the "half bandwidth" that is the full width of the band at half-power or half of the peak transmittance points specified in either wavelength units or in percent of center wavelength. Another common measure of a bandpass filter is the "half-power point" that is the wavelength at which a filter is transmitting one-half of its peak transmission. For example, for a bandpass filter with a peak transmission of 80 percent, the wavelengths at which it transmits 40 percent are the half-power points.

In certain aspects of this invention, illuminators utilize filters that can transmit a single wavelength, alternatively a narrow bandwidth, or even a wider bandwidth radiation. Novel aspects of devices useful for electromagnetic therapy permit rapid, reproducible control of characteristics of beams of radiation. Illuminators of this invention include sources of electromagnetic radiation (including visible radiation "light") that incorporate simple, reliable means for producing beams of radiation having desired wavelengths and/or other characteristics. A source of broad-band electromagnetic radiation produces radiation having a wide range of wavelengths, including those desired. One or more filters placed in the path of the radiation can attenuate certain wavelengths that are not desired, permitting desired wavelengths to pass through the filter and directed to a target. The wavelengths of radiation that pass through the attenuator ("filter") have a characteristic spectrum, depending upon the properties of the attenuator. It can be desirable to rapidly, slowly, and/or controllably change the wavelength, wavelength bandwidth characteristics, wavelength variability over time, polarization, and/or other variables to provide pulses of radiation, and to direct beams of radiation to a desired, localized target area. Means are provided to supply radiation, to attenuate radiation, to direct and shape a beam of radiation, and provide a pulsatile beam having desired pulse duration and frequency to suit a particular purpose.

Systems are provided to coordinate the production of one or more beams of radiation and to direct beams independently of one another. In some of these embodiments, the characteristics of multiple beams of electromagnetic radiation can be regulated separately.

One purpose of filtering to specific narrow bandpass characteristics is to provide radiation that interacts with particular biologic components (e.g. nerve, muscle, blood vessels, blood, connective tissues, etc), specific chemical or molecules, or a wavelength specific receptor. The ability to select both a desired wavelength and bandwidth can permit a rapid and efficient means of delivering electromagnetic radiation to an area or volume of tissue or other material in a reproducible fashion.

Radiation can be used to treat pathophysiological conditions, such as those caused by diseases or disorders. Physiological responses to electromagnetic radiation of different frequencies is variable and can result in different effects. For example, ultraviolet radiation of wavelengths in the range of about 200 nanometers ("nm") to 300 nm (ultraviolet wavelengths) can be used for sterilizing wounds or other physical objects, and infrared radiation of wavelengths longer than 700 nm (or 770 nm, according to some references) may be used to heat tissues. Each wavelength of the spectrum from 200 nm to about 1600 nm or more can be absorbed by tissues differently to provide different therapeutic responses. Simultaneous application of two or more wavelengths can be used to augment the response that would have been effected by application of a single wavelength. Because of the variability of each subject (animals and human), the ability to select specific wavelengths for that individual is desirable.

A Source of Electromagnetic Radiation

Sources of electromagnetic radiation useful for the methods of this invention are not dependent upon any particular source for operation. Each type of source (e.g. tungsten, tungsten-halogen, arc, gas discharge, broad spectrum light emitting devices "LEDs", and the like) has a spectral output that may be useful for various therapeutic applications. Incandescent lamps can provide desirable ranges of wavelengths, can be found in a variety of configurations, can be inexpensive and readily available. Arc lamps provide radiation containing wavelengths from ultraviolet through infrared that can be used as a source for a filter-based system that can deliver a narrow bandwidth, selectable over a wide range of wavelengths in the spectrum. Gas discharge lamps can supply high power pulses. Some lamps, such as commercial tungsten-halogen reflector lamps and arc lamps can be pre-focused a beam of electromagnetic radiation such that a minimum of lenses are required in the optical path. Reflector lamps can be useful in situations in which a light-weight, portable device is desired.

B Filter Based Selection of Wavelength and Bandwidth Characteristics

In some embodiments, illuminators include filters for controlling the output of electromagnetic radiation. In several embodiments of this invention, the means for controlling the output comprises an attenuator, dichroic filter or series of attenuators or dichroic filters. As used herein, the term "dichroic" means a filter or attenuator that passes certain wavelengths of radiation based upon the wavelength of that radiation. It can be appreciated that any of the properties of an output beam can be controlled and/or selected, either to select a fixed characteristic (wavelength, pulse frequency, intensity, wavelength variability, and the like) or one that varies as desired over time.

A plurality of filters can be used to adjust the bandwidth of the output radiation beam. In certain embodiments, a filter assembly comprises a series of individual filter elements, each having a transmission maximum at a certain wavelength. This wavelength is termed the "peak", "central", or "mode" wavelength. Additionally, each filter element has a certain range of wavelengths that can pass through in sufficient amount to be useful for the intended purpose of the illuminator. The wavelengths that can pass through a filter element is termed the "bandwidth" or "wavelength range". For certain filter elements, the bandwidth can be relatively narrow, that is, the peak wavelength and only a relatively narrow range of wavelengths on either side of the peak can pass through in significant amounts. In contrast, for other filter elements, the intrinsic absorptivity of the filter material is such that a relatively wide range of wavelengths can pass through in significant amounts. Such filters are herein termed "wide bandwidth" filters.

Many types of filters are available, and any type of filter material can be used that is compatible with the types of electromagnetic radiation, the other components of the system, and the ultimate use of the illuminators. For example, plastic, glass, quartz, resin or gel filters can be provided in sizes that can be adapted for use in a variety of configurations. In certain embodiments, filter elements can be made of a base material and then provided ("doped") with a material suitable for controlling the radiation emitted from the illuminator.

Once manufactured, a plurality of filter elements can be arranged in an array, in linear or variable relation to each other. For example, a series of filters can be arranged linearly, to provide a series of filters having progressively increasing (or decreasing) peak transmission wavelengths. Alternatively, a linear array of filters can be provided in which certain peak wavelengths are clustered, that is, not necessarily in progressively increasing (or decreasing) peak transmission. In certain other embodiments, filter elements can be arranged in a circular or ovoid fashion on a rotating disk. Thus, when the disk rotates and/or translates relative to a radiation source, the bandwidth characteristics of the radiation can be selected. Alternative embodiments of this invention utilize a series of fixed filters which allows selection of spectral transmission based upon the location of the filter assembly relative to the beam of radiation passing through. Alternatively, a single filter can be manufactured that has bandwidth characteristics controlled by way of example, an externally applied electrical field.

Regulation of the peak wavelength can be readily accomplished using dichroic filters. Filters having selected peak wavelength bandpass characteristics are known in the art, and can be obtained, for example from Ocean Optics, Inc. Filters can be made using precision lithography, such as used in the semiconductor manufacturing industry.

The "bandwidth" of a filter assembly is the range of frequencies (wavelengths) that pass through a filter. A band pass filter has a transmission that is high for a particular band of frequencies and with a lower transmission of frequencies above and below this band. The width or narrowness of the band for frequencies transmitted through a filter is often measured by the "half bandwidth" that is the full width of the band at half-power or half of the peak transmittance points specified in either wavelength units or in percent of center wavelength. Another common measure of a bandwidth filter is the "half-power point" that is the wavelength at which a filter is transmitting one-half of its peak transmission. For example, for a bandwidth filter with a peak transmission of 80 percent, the wavelengths at which it transmits 40 percent are the half-power points.

Color is an attribute of visual experience that can be described as having quantitatively specifiable dimensions of hue, saturation, and brightness or lightness. The visual experience also can include other aspects of perception, including extent (e.g. size, shape, texture, and the like) and duration (e.g. movement, flicker, pulse duration, and the like). Color names (e.g. blue, turquoise, etc.) are often used to describe various wavelengths or groups wavelengths of visible light. The radiation used in scientific, industrial, and medical instruments is generally specified by the wavelengths transmitted and the proportions of each wavelength within the active area. The use of color names can be a convenient way to express the appearance of the light. For purposes of these descriptions, color names can be used to convey an approximate range of wavelengths used. Color names often describe combinations of wavelengths of radiation from differing portions of the visible spectrum. The color to wavelength conversion identity varies slightly from the various resources. One source, Van Nostrand's Scientific Encyclopedia, Third Edition, lists the conversion as:

| Violet | 390–455 nm |
| Blue | 455–492 nm |
| Green | 492–577 nm |
| Yellow | 577–597 nm |
| Orange | 597–622 nm |
| Red | 622–770 nm |

However, other reference books recite other wavelength ranges for the above colors. Thus, we do not intend that each color name be provided with an exact wavelength or bandwidth characteristic. Rather, each of the colors described herein is intended to be a guide for use of the devices of this invention. For example, for therapeutic purposes, the color "violet" may contain amounts of longer, blue wavelengths, and may also include certain amounts of shorter wavelengths, in the ultraviolet range. Similarly, the color yellow may contain certain amounts of green and/or orange light. Moreover, other colors described by their common names may include greater or lesser amounts of other, wavelengths.

Some commonly named colors include two or more wavelength bands of light. Magenta, for example, has two peaks, one in the violet region and another in the red region. Purple has peaks similar in wavelength to Magenta but has higher violet transmission.

Perception of a given color may result from combinations of wavelengths added together. The most common combination is red+green+blue. These three colors are used in differing proportions in computer monitors and displays to create the colors available on the display. Other combinations of filters maybe used in parallel to produce perceived color. The printing industry adapts to varying ink properties as a routine matter.

1. Filters

When used for therapeutic purposes, a purpose of filtering radiation to specific narrow bandwidth characteristics is to provide radiation having wavelengths that interact with particular biologic components (e.g. nerves, muscles, blood vessels, blood, etc), specific chemicals or molecules, or other wavelength-specific receptors. By selecting the desired wavelength(s) and the bandwidths of wavelengths can permit a rapid and efficient means of delivering a reproducible electromagnetic stimulus to an area or volume of tissue or other material.

In certain embodiments, our invention utilizes filters that transmit a single wavelength ("central wavelength") or narrow bandwidth of wavelengths. One aspect of our filter design permits control of the width of the bandwidth by means of moving the filter in two directions with respect to the radiation path. Movement of the filter relative to the radiation source in one direction controls the peak, center, mean or mode wavelength, and movement in another direction can provide radiation having differing bandwidth ranges.

In other embodiments of this invention, a central wavelength can be used and a time-dependent variation in wavelength around the central wavelength can be used ("wavelength variation"). By changing the magnitude and/or frequency and/or the rate of change of wavelength around the central wavelength, desired therapeutic effects can be elicited.

In certain embodiments, a fixed aperture that limits the transmission of radiation to a well-defined area such that the mix of wavelengths transmitted represents the sum of filter elements within that aperture. The amount of radiation at the peak transmission wavelength may diminish as additional filter elements of differing wavelengths are introduced into the radiation path. This design is simple and can use any desired aperture area practical.

2. Linear Filter Arrays

In certain embodiments, a series of filters having different fixed transmission characteristics may be placed between a radiation source and one of the waveguides. These filters may be used to select the desired ranged of wavelengths or to exclude large segments of the spectrum, such as, for example, infrared blocking filters.

In other embodiments of this invention, a linear filter, such as a Schott Veril 60, may be manufactured such that the transmission spectrum continuously changes with respect to the position along the filter array. The variable spectrum characteristics of the filter array are accessed as desired by moving the filter array along the variable wavelength axis through the radiation beam in the illuminator section by means of a mechanism. The mechanism must allow repeatable motion when driven manually or by a motor. One embodiment of this apparatus uses a leadscrew and carriage assembly to move the filter. Another embodiment uses a rack and pinion type of mechanism. A linear version of the circular variable filter described below may be manufactured as either an array of individual filters or as an array that permits changes in the width of the spectrum and maximum transmitted wavelength by moving the filter array in two axes transverse to the radiation beam.

It other embodiments, "wedge" type filters can be used, in which an absorptive medium is provided on a substrate. One portion of the wedge typically has a thinner layer of absorptive medium, and another portion typically has a thicker layer of absorptive medium. An interference pattern can be generated by wavelengths of radiation, so that radiation emitted can have different wavelengths, depending upon the thickness of the layer of absorptive material. Certain filters useful for the devices of this invention can be obtained commercially from Ocean Optics, Inc. Thus, in certain embodiments, two or more wedge filters can be place near one another so that the radiation emitted by both filters can be collected and used. However, the above description is not intended to be limiting, rather any available filter types can be used.

In certain embodiments, arrays of small filter elements can be provided that have small size (about 1 μm on a side) and manufactured using photolithographic methods, as used in the semiconductor manufacturing industry. For radiation having short wavelengths, (e.g., 200 nm), the size of the filter elements can be even smaller (e.g., 200 nm). Planar arrays of such filters can have large numbers of individually manufactured filters, and, if desired, each can have different bandpass characteristics. Certain of these types of filter arrays can be obtained from Ocean Optics, Inc.

Filters may be fixed in place or moved into or out of the beam by mechanisms provided for that purpose. The characteristics of the filters are selected for the requirement of the system. For example, a filter may pass two or more fixed wavelengths of radiation through one illumination section which is then combined with a variable wavelength radiation from another illumination section to provide more specific narrow wavelengths than the number of illumination sections. Additional filters may be selected or automatically placed in the radiation path as designed into the particular mechanism. Some example of the filter types are narrow band, cut-off, or bandwidth filters.

Variable filter used to select the wavelength or spectrum of wavelengths for each illumination section may be created by a variety of methods and physical shapes and sizes. The filter media maybe of any type that has the desired radiation transmission characteristics. Some example filters include gel filters, interference filters, dichroic filters, substrate filters or other types known in the art. The geometry of the illumination beam and the shape and position of filters can be adjusted to obtain radiation having desired spectral characteristics.

3. Circular Filter Arrays

Circular filter arrays can be used that have one or more patterns of filter elements or materials that allow transmission of different wavelengths depending on the relative rotational position of the circular filter array and the source beam. The filter array may be rotated to discrete angular positions manually or motorized for remote control. A means of repeatedly returning to a desired angular position can be provided by a dial or by a memory element associated with the motorizing system. Some examples of a motorizing system are a stepping motor with a means of initializing the angular position, or, a servo motor with an encoder which provides initializing information.

Dimensions of the beam of radiation relative to the active circumference of the illumination section can contribute to the spectral distribution of the radiation entering the waveguide. In some embodiments, a variable filter pattern can comprise an annulus that has variable wavelength transmission along the circumference that passes through the illumination path as the filter is rotated about its axis of rotation. One result can be that each angular position corresponds to a different specific narrow spectrum of wavelengths. For filter arrays having continuous and monotonically changing transmission along the circumference of the array, the width of the radiation spectrum emerging from the illumination section is determined by the ratio of the active circumference to the diameter, or width (for non-circular entrance ports) of the beam entering the waveguide. A filter array may also be manufactured that comprises a series of discrete filter elements or materials which are accessed by rotation of the filter disk.

In certain embodiments, a process permits manufacturing of a pattern such that the transmission characteristics of any angular and radial position can be selected. The pattern may be such that the area of each pattern element is small relative to the active area of the beam. This allows the center of rotation of the circular filter to be moved relative to the beam to provide differing transmission characteristics based on both active radius and angular position. For example, the outer radius portion of the pattern area may have a constant linear variability, for example, from 400 nanometers ("nm") to 1000 nm, that provides a narrow spectrum of wavelengths to emerge from the illumination section, while the inner portion of the pattern area may provide a mixture of elements that combine to provide a broader spectrum of wavelengths to emerge from the illumination section. Thus moving the center of rotation and angle of the filter relative to the radiation beam can select a specific narrow wavelength or a wider spectrum of wavelengths. This ability to select center wavelength and spread of wavelengths allows the system to provide additional control over the radiation emerging from the illumination section.

Illuminators of this invention may have a fixed aperture that limits the transmission of radiation to a well-defined area such that the mix of wavelengths represents the sum of filter elements within that aperture. The amount of radiation at the peak transmission wavelength may diminish as additional filter elements of differing wavelengths are introduced into the radiation path. This design is simple and can use the maximum aperture area practical. In other embodiments, an aperture having variable area maybe constructed that may increase in size if desired to allow additional radiation of differing wavelengths to be added to the original beam. Conversely, if it is desired to provide a narrower band pass, the aperture can be decreased in size to exclude undesired wavelengths from passing. This design can be used to keep the amount of radiation at peak transmission wavelengths approximately constant while adding radiation of differing wavelengths.

Selection of peak wavelength, bandwidth and/or intensity can be controlled by the use of a plurality of shutters positioned relative to a filter array. By opening certain shutters that are positioned corresponding to a desired peak wavelength, a beam of radiation can be captured that has that selected peak wavelength. One can open up shutters corresponding to higher, lower, or both higher and lower wavelengths to permit the passage of radiation having a broader bandwidth. Alternatively, one can open up a plurality of shutters corresponding to a peak wavelength to increase the intensity of radiation in an output beam. A plurality of peak wavelengths can be selected to provide multiple wavelength output beams. It can be readily appreciated that numerous variations of the above can be used to provide a large number of possible output beams.

The types of shutter mechanisms used are not crucial. In certain embodiments, one can use mechanical shutters that can be retracted to open up an aperture. In other embodiments, an array of mirrors can be used to reflect the beam of radiation toward a particular location. In still other embodiments, a shutter array can incorporate an electro-optical device, including by way of example only, liquid crystal devices (LCDs), Pockels cells, Kerr cells and other optical devices. In a shutter array, control over individual shutters can be accomplished using mechanical or electrical signals, and those can, in certain embodiments, be controlled by a computer program.

C Pulsed Illuminators

In addition to providing radiation having controlled wavelength and bandwidth characteristics, the radiation may be provided in a continuous or pulsed fashion. Pulsing radiation can either provide a frequency of radiation that can be absorbed by different targets differently to achieve a desired degree of stimulation, or alternatively as a means for controlling the total dose of radiation emitted by the device. To provide pulses of radiation, any suitable mechanism that can regulate the pulse width (duration), the frequency, or the pattern of radiation pulses can be used. For example, in several embodiments, radiation can be passed through a shutter or chopper system to provide the aforementioned radiation as pulses at variable frequencies. In a circular chopper, a disk of opaque material having holes, slits, slots, or areas of transparency can be rotated about an axis perpendicular to the plane of the disk. A portion of the rotating disk can be placed in a beam of radiation, and during the time that a hole or transparent area is in front of the beam, the beam can pass through the disk, thereby providing the desired radiation. When an opaque portion of the disk is in front of the beam, the radiation is blocked from passing through. Examples of choppers or interrupters suitable for use with the methods of this invention are described in the co-pending United States Utility Patent Application titled "Multiple Wavelength Illuminator," Allan Gardiner and Constance Haber, Inventors, filed concurrently, incorporated herein fully by reference. Advantages of pulsed radiation include increased efficacy of electromagnetic radiation therapy. For example, the use of different frequencies of radiation pulses has been demonstrated to affect nerve cells differently from muscle cells. The selection of the wavelength and frequency of the radiation can be based upon methods developed for each application.

A chopper or shutter mechanism maybe placed in the radiation path of an illumination section to provide intermittent pulses. A chopper can be desirable if it transmits all of the radiation in the open state. The number of apertures in the chopper and the rotational speed of the chopper can determine the pulse rate. Low pulse rates may also be obtained by oscillating the chopper aperture across the radiation beam. The rate that the chopper is moved may be varied over time to produce a profile of radiation intensity vs. time. A single chopper may be placed such that two or more radiation sources pass through the chopper. The placement of the radiation sources, the placement of the center of rotation of the chopper, and the number of apertures affect the relative timing of the pulses for each radiation source. Certain of these embodiments can have four apertures and two radiation sources placed symmetrically around the center of rotation such that the initiation of each pulse is concurrent for both entrance ports. Electro-optical shutters, including by way of example only, LCDs, may be used in place of the chopper wheel to achieve similar results and add independent initiation of pulses and/or pulse profiling.

It can be readily appreciated that a chopper or an electro-optical mechanism can be designed to provide any desired pattern of pulses. For example, in one series of embodiments, a circular disk having transparent areas arranged in arcs around the disk can be used in situations in which it is desired to have a repeated pattern of pulses. It can be appreciated that the arc length of a transparent area and the rotation speed can determine the duration and frequency of pulses. However, by providing transparent areas of differing configurations, for example, one having a relatively long arc length, and another having a relatively shorter arc length, a pattern of long and short pulses can be provided. It can also be appreciated that providing transparent areas that are equidistantly arrayed about the disk can provide a pulse frequency that is substantially constant. However, by providing transparent areas of differing distances from one another, one can select the pattern of radiation pulses.

A pulse can have an abrupt onset or a ramped onset. By providing transparent areas that have a clean, or "sharp" edge, the onset of a pulse can be abrupt. However, by providing a wedge-shaped slot, or alternatively, a gradient transition between opaque and transparent areas, the onset of the pulse can be varied. Moreover, in these embodiments, one can appreciate that providing a slower rotation can provide a prolonged transition period between "off" and "on" parts of the duty cycle. Although different pulse patterns are described for mechanical choppers, it can be readily appreciated that electro-optical choppers can be used that can provide a wide variety of pulse patterns.

One or more sensors may be added to monitor the beginning of radiation pulses and functionality of the illumination section. Many devices and methods are available to determine the start time of a pulse. For example, a fiberoptic pickoff may be mounted next to the waveguide entrance port. Output of this pickoff may be used to monitor the wavelength and intensity of the radiation passing through the illumination section when coupled to appropriate sensors. The output may be passed through a narrow-pass filter to initialize a reference position or confirm the positional repeatability of the system. Another example is a sensor to determine the location of the chopper apertures relative to the entrance ports. Pulse rate can be adjusted by the chopper motor controller circuitry based on output of an encoder integral with the chopper motor. The accuracy of the radiation pulse rate can depend upon the control circuitry and may have different ranges of acceptable accuracy for different applications.

In one series of embodiments of devices include a radiation source, filters and an optical system to deliver the filtered radiation to a waveguide, such as a fiberoptic element. Multiple radiation sources can be combined in the fiberoptic cable system and delivered to one or more radiation delivery ports. The routing of fibers determines the proportion of each wavelength at each delivery port.

D Multiple Beam Illuminators

Devices of this invention can utilize two or more radiation sources that may be of the same or different types. Typical radiation sources include incandescent lamps, arc lamps, and strobe lamps for systems that are intended to provide selectable wavelengths. Narrow spectrum devices, such as lasers or LED's, may also be used when the bandwidth dispersion is desirably narrow. Gas discharge lamps can have several wavelengths that are emitted which may also be useful, such as combining UV radiation with visible and/or infrared radiation.

A radiation source optical system may be as simple as a mirrored reflector behind the radiation source which can focus the radiation beam onto the waveguide. Additional optics may be incorporated as desired for the particular illumination system. For example, a broad area source, such as a strobe, may use a collecting or collimating lens system between the source and the filter. The characteristics of the radiation source reflector may affect the operation of the system. For example, a reflector maybe used which allows a high proportion of the infrared (heat) emitted by the radiation source to be transmitted away from the filter and waveguide.

E Waveguide/Fiber-Optic Cable Assembly

Waveguides or fiberoptic cable assemblies can consist of multiple entry ports and one or more exit ports. Routing of the fibers can determine the proportion of radiation from each entry port to each exit port. The material of the waveguides or optical fibers is selected to permit passage of the desired wavelengths. For example, glass fibers may be used for visible and infrared radiation (400–1000 nm) while other materials, such as quartz fibers may be selected for ultraviolet radiation (200–400nm). Many configurations and materials, including liquids, are possible. In certain embodiments, there can be two entrance ports and two exit ports. The fibers can be routed to provide one-half of the radiation from each entrance port to be directed to each exit port. This arrangement can provide the user with two radiation sources with similar multi-wavelength output.

In other embodiments, alternate fiber routing configurations may be used to provide different ratios of input to output. For example, a third entrance port may have a radiation source that does not utilize a filter system. This illumination section may provide output from a simple lamp to provide general illumination or may provide a source of ultraviolet radiation that can pass directly into the entrance port of the waveguide with little attenuation.

The output beam of electromagnetic radiation can be provided in a number of different desired shapes and configurations. For example, for certain therapeutic uses, it can be desirable to provide beams having rectangular, triangular, polygonal, circular, oblong, annular, or other desired shape. By arranging waveguides in any of the above configurations, a desired beam can be provided. Randomizing the waveguides can provide an output beam in which the different wavelengths and/or bandwidths are distributed randomly within the area of the output beam. If desired, a defined array of wavelengths and/or bandwidths can be provided by maintaining a desired or non-random arrangement of fibers. By providing flexible waveguides, different beams can be separately directed at different desired locations.

F Analysis of Temporal Data and Therapeutic Responses

Analysis of spectral and timing data from illuminators of this invention can be performed using a computer and a software package, either designed specifically for the purpose, or using commercially available software. A data filter in a commercial application including joint time frequency analysis using Fast Fourier Transform "FFT" as well as other deconvolution methods can permit correlation of spectral and time related data (pulse or chop) and physiological effects of electromagnetic radiation. In certain embodiments, measurements involve monitoring a radiation signal using the chopper or electro-optical shutter to expose a part of a subject's body to radiation of a known wavelength, bandwidth, pulse width, intensity, and pulse frequency. Simultaneously or at intervals, one can monitor effects of such radiation using, for example, the surface Electro Myogram (sEMG), electroencephalogram (EEG), evoked responses and the like. An analog input from a monitoring device and/or from a light source can be provided into the computer, and the phase and frequency domain of the signal relative to output of chopper signal can be determined using, for example LabView™ software. This can be used to determine the signal strength and the transit time for the signal to travel to the sensor is. The system consists of a chopper, which can be run at a frequency of about 1 Hertz (Hz) to about 1000 Hz. In alternative embodiments, the chopper can operate at a frequency of between about 1 Hz and about 500 Hz, and in still other embodiments from about 5 Hz to about 100 Hz. Using pulsed illumination, a system can detect the presence of signal and the phase differences between remote locations on the body. This can permit comparison of transmission capability through excitable tissues, such as nerves, muscles, and connective tissues, in conditions such as, for example, diabetic neuropathy and other nervous disorders, especially disorders of the spine. Normal physiological responses can be obtained by studying subjects without specific disorders, or by studying unaffected organ and tissues of normal subjects.

Additionally, by comparing the above-obtained normal results with those obtained from subjects having specific disorders of excitable tissues and organs, improved diagnosis of those conditions can be provided. Additionally, by monitoring a subject's responses to electromagnetic radiation therapy over time, improved evaluation of the progression and/or treatment of those disorders can be provided. Additional discussion of specific disorders of excitable tissues is provided in the U.S. Provisional Patent Application titled: "Therapeutic Methods Using Electromagnetic Radiation," Constance Haber, D.C., and Allan Gardiner, P. E., inventors, filed Jun. 26, 2001, incorporated herein fully by reference.

G Use of Multiple Beams of Electromagnetic Radiation

One can use different beams of radiation to achieve a desired therapeutic aim. In some embodiments, the beams can have the same or different relative intensities, peak wavelength, bandwidth, pulse duration, pulse frequency, and/or polarization. For example, one can expose a proximal portion of a nerve to radiation having relatively higher intensity than a more distal portion, or vice versa. Electromagnetic radiation can be provided continuously, or in short bursts, termed "pulses", having known as frequencies or duty cycles. Pulses can be varied according to their frequency and duration. For certain uses, it can be desirable to independently vary the pulse rate and duration on each beam. Therefore, it can be advantageous to provide separate control over each of the above-identified variables, including central frequency, wavelength variation, pattern of wavelength variation, pulse duration, intensity, and the like. In certain embodiments, control over the above variables can permit a practitioner to "entrain" different physiological responses, thereby improving the efficacy of therapy.

It can be desirable to expose nerves to localized or "focal" beam of radiation. In other embodiments, it can be desirable to use beams of radiation that have different shapes, including, circular, annular, rectangular, triangular, linear and the like. Devices for producing such varied beams are disclosed in U.S. Provisional Patent Application titled: "Multiple Wavelength Illuminator", Allan Gardiner et al., inventors, filed concurrently, herein incorporated fully by reference.

In certain embodiments of this invention, it can be desirable to treat a nerve across or along the nerve distribution by moving the location of exposure. One can begin at a proximal portion of a nerve distribution and move the site of exposure more distally, or alternatively begin at a more distal site and move the site of exposure more proximally. In other embodiments, it can be desirable to expose a plurality of sites along a nerve distribution. For example, one can expose the proximal most point (spinal exit) of the arm, another site in the intercubital fossa to expose the median nerve of the arm, and then a more distal site in the hand. If desired, one can progressively move the site of exposure between proximal and more distal sites to treat a nerve along a larger portion of its distribution. In other embodiments, it can be desirable to treat multiple sites simultaneously.

The nervous system includes distributions of nerves to each side of the body. However, nerve distribution to one side of the body can arise from both sides of the nervous system. Typically, somatic innervation arises from the opposite, or contralateral, side of the nervous system. Thus, innervation of the left side of the body can arise from the right side of the brain or spinal cord. Thus, affecting one side of the body can affect sites on the contralateral side of the body. Additionally, affecting one side can affect sites on the same ("ipsilateral") side of the body. Thus, in certain embodiments, it can be desirable to stimulate either one side, the other side, or both sides of the body to achieve a desired therapeutic result.

The amount of electromagnetic radiation reaching a tissue can depend on the wavelength of the radiation, the depth of the site to be affected and the opacity of overlying tissues to the wavelength used. Thus, to expose a proximal portion of a nerve, where it exits the spinal column, may require higher absolute intensity than that required to stimulate a more distal portion of the same nerve that is located near the skin. Moreover, electromagnetic radiation having longer wavelengths, in general, can penetrate more deeply into a tissue than can radiation having shorter wavelengths. Thus, if the wavelength of radiation used is not critical, it can be desirable to use longer wavelengths to treat deeper structures. However, in certain embodiments, it can be desirable to expose deep structures to relatively short wavelengths, and in these situations, it can be desirable to use higher intensity radiation to provide a desired degree of exposure. It can also be desired to vary the intensity of radiation of each of two or more wavelengths to achieve desired therapeutic end points.

II Principles of Activity of Excitable Tissues

Although the mechanisms for therapeutic effects of electromagnetic radiation are not known with certainty, one hypothesis is that electromagnetic radiation can affect nerves, muscles, or structures that can conduct electrical charges, including tendons, ligaments, extracellular fluid and the like. According to an hypothesis as described and applied to nerves, electromagnetic radiation of certain wavelengths maybe absorbed by nerves or other nearby tissues, altering the activity of the nerve. Depending on the nerve or other type of excitable tissue, the type of neurotransmitter used, the types of transmitter receptors activated, and the wavelength of radiation used, the absorbed energy can either activate or inhibit action of those tissues. Moreover, mechanisms for activation and inhibition of nerves and muscles by electromagnetic radiation are not known with certainty. According to one theory, when electromagnetic radiation is absorbed, the energy from that radiation maybe manifested by an alteration of one or more of the fundamental mechanisms that underlie the function of a nerve or nerve cell, a muscle or muscle cell, or other excitable cell or tissue. Because an excitable tissue typically exists within a conductive medium, such as extracellular fluid, electrical events can be propagated to sites distant from that tissue. Additionally, the electrical and/or ionic state of the medium can affect the responsiveness of an excitable tissue. Thus, according to this hypothesis, electromagnetic radiation can affect excitable tissues via direct action locally, or via indirect action on the state of the surrounding tissues and/or medium.

Motor nerves can regulate the functions of effector organs, such as muscles, exocrine and endocrine secretory cells and the like. Motor nerves can arise in the central nervous system in the brain, spinal cord, or peripheral ganglia. Sensory nerves can monitor the states of an organ, tissue or cell. When activated, sensory nerves can mediate and transmit sensations of pain, kinesthesia (body position and motion), and can participate in numerous reflexes, including postural and autonomic reflexes. Symptoms of many disorders include pain as a prominent feature. Thus, one aim of electromagnetic radiation therapy is in the reduction in pain through alterations in the function of sensory nerves or other structures that can affect sensory nerve function.

Sensory nerves also can assist in control of skeletal muscles. For example, within skeletal muscle fibers, smaller specialized muscles exist, known as gamma fibers. Gamma-fibers include a specialized stretch receptor that is sensitive to the overall length of a gamma fiber. When the gamma fiber is stretched, an associated gamma-sensory neuron can transmit a signal to the spinal cord, to a primary (or "alpha") motor neuron innervating that muscle. Increased activity in a sensory gamma-neuron can stimulate the alpha motor neuron to activate the muscle, causing contraction and thus providing a force to counteract the stretch placed on the muscle. This "stretch reflex" is common in postural muscles, and is a prominent mechanism responsible for maintaining proper muscle tone around a joint such as shoulder, vertebrae or hips, and thereby maintain posture.

The degree of sensitivity of the gamma-loop can be regulated in part by motor neurons that innervate the gamma muscle fiber ("gamma-motor neurons"). When a gamma-motor neuron is activated, it can cause contraction of the gamma muscle fiber, shortening the gamma fiber and decreasing the amount of stretch of that fiber and thereby decreasing the stimulation of the gamma sensory fiber. Thus, when the gamma muscle fiber is short, the gamma reflex mechanism is relatively insensitive to stretch, and when the gamma fiber is relaxed and the gamma-sensory neuron is relatively stretched, the reflex mechanism is relatively sensitive to further stretch. Thus, the gamma fiber, the gamma stretch receptor, and the gamma motor neuron comprise a "gamma loop" that aids in maintaining posture through the stretch reflex.

Alterations in the relationships between gamma-loops and the skeletal muscle in which they exist can lead to abnormalities of posture, and to pain. According to one hypothesis, an imbalance between the gamma-loops and the normal, voluntary control of skeletal muscle can lead to muscle spasm, pain, and other symptoms.

Sensory and motor nerves can interact with each other through less specific interactions, involving additional levels of neural integration, through brain structures such as the hypothalamus, thalamus, reticular activating formation, cerebrum and others.

Thus, in certain embodiments of this invention, one goal of therapy with electromagnetic radiation is restoration of normal physiological balance between different aspects of the nervous system and the musculature. The description that follows is intended to illustrate some of the principles of physiology of excitable tissues, using nerves as an example. The descriptions are not intended to be comprehensive. Further discussions of the physiology of nerves and the chemical transmitters that are involved in neurotransmission can be found in Goodman and Gilman's The Pharmacological Basis of Therapeutics, Ninth Edition, McGraw Hill, 1996, incorporated herein fully by reference.

A Neuronal Physiology

Physiological mechanisms that underlie neuronal function have been subject of numerous studies for many years. Neuronal function can be altered by affecting the concentrations of ions inside and outside cells, the conductance of the nerve to those ions, the release of neurotransmitters, the sensitivities of neurons to those transmitters, or other factors. Typically, at rest, nerve cells ("neurons") and muscle cells ("myocytes") can have a net negative charge in their interiors, relative to the outside, or "extracellular" milieu. Neurons typically have positive charges in the form of positively charged potassium ("$K^+$") ions and negative chloride ("$Cl^-$") within the cell. In contrast, the extracellular milieu comprises a positively charged sodium ("$Na^+$") ions and negatively charged Cl⁻ ions. The concentration of $K^+$ ions in the extracellular space typically is lower than that in the intracellular milieu, and $Na^+$ ion concentrations within neurons is typically lower than that in the outside milieu. Thus, there is a concentration gradient for $Na^+$ from the outside of the cell to the inside, which, if the membrane were permeable to $Na^+$ ions, would result in the flow of $Na^+$ into the cell. Similarly, there is a concentration gradient for $K^+$ ions, from the inside of the cell to the outside, which if the membrane were permeable to $K^+$ ions, would result in the flow of $K^+$ ions outside the cell. Under resting conditions, however, the permeability of neuronal cell membranes to $K^+$ ions is not the same as the permeability of the neuronal membrane to $Na^+$. Rather, on average, $K^+$ leaves the cell more easily than $Na^+$ enters the cell, resulting in a net decrease in intracellular positive charges. This results in a negative or "resting potential" or voltage difference from the inside of a cell to the outside of the cell. Cells that typically can have negative resting potentials include neurons, muscle cells and many glandular cells. This resting state is termed "polarization."

Activation of nerves, muscles, and in some cases, glandular cells, can result from an alteration in the flow of ions across the cell membrane. For example, mechanical stimulation of most nerves can produce an increased (less negative) intracellular potential. This process is termed "depolarization." If the increase in potential is sufficiently large, the membrane potential can reach a "threshold" voltage, at which Na+ion channels can open, permitting Na+ ions to flow into the cell, further increasing the intracellular voltage. In nerves and muscle cells, this process is termed an "action potential." Action potentials are important mechanisms for nerve transmission ("neurotransmission"). Similarly, in many types of muscle cells, including cardiac and skeletal muscles, action potentials can produce changes in calcium ("Ca+") ion movements and activation of the muscle fibers, causing contraction.

It can be appreciated that changing the ionic composition of the extracellular milieu can alter the gradients of ions across a cellular membrane. Thus, by increasing the concentration of Na+ ions in the extracellular milieu, the gradient for Na+ can increase. Then, if Na+ channels open, more Na+ is available to enter the cell, thereby increasing the amount of positively charged ions within the cell. Similarly, alterations in concentrations of other ions in the extracellular milieu can alter the movement of those ions into and/or out if cells. According to this hypothesis, because most parts of the body are in electrical contact with each other, via electrically conducting fluids containing ions, alteration in the electrical and/or ionic state of one tissue can affect the electrical and/or ionic state of another tissue. Thus, electromagnetic radiation can have numerous effects on excitable tissues at the site(s) of absorption of the radiation, and at sites remote from the site(s) of absorption.

B Synapses and Neurotransmitters

Activation of a nerve or muscle can be initiated by the secretion of specific chemicals, herein termed "neurotransmitters" between neurons or between a neuron and a muscle cell. One type of junction between nerve cells is termed a "synapse" and a corresponding type of junction between a nerve and a muscle cells is termed a "neuromuscular junction." Conduction of electrical activity between cells across synapses or neuromuscular junctions can be accomplished by the secretion of one or more neurotransmitters by one cell and the attachment of those neurotransmitters onto specific receptors within the membrane of the neighboring cell. Binding of neurotransmitter can either cause depolarization of a cell membrane, or alternatively can further polarize the cell membrane. Depolarizing neurotransmitters include acetylcholine, ("Ach") which is a widely distributed transmitter in cholinergic nerves. Many neurons are sensitive to the neurotransmitter acetylcholine ("Ach"), which is responsible for many neurophysiological phenomena, including contraction of voluntary muscles and many central nervous functions, including ganglionic transmission and cerebral transmission.

Other nerve types include the adrenergic nerves, which can use epinephrine (adrenalin, "EPI"), nor-epinephrine ("NE"), serotonin, dopamine ("DA") and a number of other chemical transmitters known in the art. Depending on the nerve location, the transmitter and the types of receptors involved, a nerve may be either unaffected, polarized or depolarized. By way of illustration, a resting or polarized nerve will require a certain degree of depolarization to become activated to produce an action potential. If a neurotransmitter further polarizes the nerve, resulting in a "hyperpolarized" state, it may require more of the depolarizing neurotransmitter to cause an action potential in that nerve. Conversely, if a second type of depolarizing transmitter is present, then a smaller amount of the first depolarizing transmitter is needed to cause the nerve to exhibit an action potential. Thus, inhibition of nerve action can be by way of hyperpolarization, whereas heightened nervous sensitivity can be caused either by increased "tone" of the transmitter system normally involved in depolarizing the nerve, or by increased release of a different, depolarizing neurotransmitter. These opposing effects of polarization and depolarization are important mechanisms involved in maintenance of normal function, or "homeostasis."

C Autonomic Nervous Systems

Many bodily functions are modulated by branches of the nervous system known as the "autonomic" nervous systems. Autonomic nervous systems can regulate gastrointestinal function, blood pressure, blood flow, body temperature control, and numerous other processes. Autonomic nervous systems can be present in an organ or tissue as two (or more) systems operating independently, cooperatively or in opposition to one another. For example, in the gastrointestinal tract, the cholinergic autonomic nervous system (generally, the "parasympathetic" nervous system) can stimulate gastrointestinal smooth muscles through the release of acetylcholine, which in those tissues, can act on a type of cholinergic receptor known as "muscarinic receptors." Stimulation of muscarinic receptors can lead to decreased heart rate, increased gastrointestinal motility, and other effects. In contrast, acetylcholine acting through another type of cholinergic receptor, the "nicotinic receptors" is involved in autonomic ganglion neurotransmission.

Another branch of the autonomic nervous system is the "sympathetic" nervous system. In the gastrointestinal tract, the sympathetic nervous system can inhibit the smooth muscle contraction caused by activation of parasympathetic nerves. Sympathetic nerves characteristically use chemicals known as catecholamines or other monoamines as neurotransmitters. Well-known catecholamines include epinephrine and norepinephrine. Epinephrine and norepinephrine can act on specific adrenergic receptor types, termed "alpha-adrenergic" and "beta-adrenergic" receptors. Activation of alpha-adrenergic receptors stimulates contraction of vascular smooth muscle, causing blood vessel narrowing and leading to increased blood pressure and/or decreased blood flow through that vessel. In contrast, activation of beta-adrenergic receptors can lead to relaxation of blood vessel smooth muscle, which, in turn can lead to decreased blood pressure and/or increased blood flow. Activation of beta-adrenergic receptors in the heart can increase pulse rate and force of cardiac contraction, effects which can lead to increased blood flow.

Norepinephrine can cause contraction of blood vessel smooth muscle, resulting in decrease in blood vessel diameter. In arteries, decreased vessel diameter can lead to increased blood pressure, decreased blood flow, or both. In veins, blood vessel contraction can lead to increased cardiac input, which can result in increased cardiac output and increased systemic blood flow. In contrast, acetylcholine acting via muscarinic receptors, can relax blood vessel smooth muscle cells, and can result in decreased blood pressure and/or increased blood flow. Activation of muscarinic receptors in the sino-atrial node of the heart can lead to decreased heart rate. Thus, the adrenergic and cholinergic systems (sympathetic and parasympathetic) can, in certain situations, tend to counteract one another, leading to opposing influences on end organs innervated by both types of neurons.

D Neurotransmitter Receptors

Within the same branch of the autonomic nervous system, different receptors and transmitters can exert competing or opposing effects. For example, norepinephrine, an adrenergic transmitter, is a potent stimulator of the adrenergic receptor type known as "alpha-adrenergic" receptors. In contrast, norepinephrine is a relatively weak stimulator of "beta-adrenergic" receptors. Unlike norepinephrine, epinephrine (also known as adrenalin), at low concentrations, is a more potent stimulator of beta-adrenergic receptors than it is of alpha-adrenergic receptors. Thus, epinephrine in low concentrations can cause vasodilation, can decrease blood pressure, and can increase blood flow. At high concentrations, epinephrine's effects on alpha-adrenergic receptors can dominate over the effects on beta-adrenergic receptors, and can cause increased blood vessel contraction and can lead to increased blood pressure.

E Peptidergic Innervation

In addition to the cholinergic and adrenergic systems, other types of nerves use peptides or amino acids as neurotransmitters. A examples of a peptide transmitter is substance P, ("SP") a member of the "tachykinin" family of peptides. SP is a transmitter of painful stimuli, and is one of the chemicals released by the active agent of red peppers, capsaicin. Other tachykinins include neurokinins A and B. Other types of peptidergic nerves use enkephalins, endorphins, vasoactive intestinal peptide ("VIP") somatostatin, calcitonin gene-related peptide, gastrin releasing peptide, and numerous other peptides known in the art. As with the sympathetic and parasympathetic nervous systems, peptide-containing nerves may have opposing or synergistic actions with those of other peptidergic nerves or with sympathetic and/or parasympathetic nerves.

In the spinal cord, painful transmission is thought to be mediated by sensory afferent nerves that use substance P (SP) as a neurotransmitter. In certain locations within the spinal cord, other nerves, using opioids such as enkephalins and/or endorphins, can interact with the afferent pain nerves. Enkephalins can decrease the activity of sensory pain nerves, and therefore, represents one physiological mechanism for reduction in pain, (also termed analgesia).

F Somatic Innervation

In addition to autonomic nerves, "somatic" nervous system is responsible for such effects as voluntary control of skeletal muscle. Somatic innervation typically can be present in a segmental pattern, that is each portion of the body is innervated by nerves arising from a discrete portion of the spinal column, usually associated with different vertebra. Thus, control of upper portions of the body are typically by way of spinal nerves exiting the vertebral column in high vertebrae, such as neck ("cervical") or chest ("thoracic") vertebrae. Lower portions of the body, such as the legs are typically innervated by nerves exiting the spinal column in lower thoracic, lumbar or sacral areas.

One common source of arm, back or leg pain can be due to mechanical compression of the spinal sensory nerves. For example, if a lower spinal nerve is exposed to pressure, that pressure can be sensed as pain, for example, in sciatica. Another source of disorders can be pressure exerted on motor (also known as "efferent") nerves. Compression of sympathetic efferent nerves can lead to disorders of blood flow. Compression of somatic nerves can lead to weakness or even paralysis.

G Activation of Nerves

Nerves can typically be activated by mechanical or chemical stimuli. Even nerves that act primarily as chemical sensors ("chemoreceptors") can be activated by mechanical stimulation, such as pressure. Activation of nerves under normal physiological situations typically can involve the stimulation of areas of the nerve termed "dendrites". When so stimulated, an alteration in a neuron's resting potential can occur, resulting in depolarization. When depolarization becomes sufficiently large, a certain voltage threshold can be reached and an "action potential" can be initiated, either within the dendrites, in the neuronal cell body (also known as the "soma") or in an axon. An action potential can be propagated along an "axon" which in motor nerves to voluntary muscles, can be 1 meter or more in length. Thus, activity of a neuron in one location can be reflected in activity at remote locations within the distribution of that nerve. Typically, a single chemical stimulus, such as that caused by a single neurotransmitter molecule, is insufficient to cause an action potential. Rather, it may be necessary for a number of receptors to be stimulated to cause sufficient depolarization to produce an action potential.

It can also be appreciated that many portions of a nerve cell can respond to depolarization. For example, mechanical or electrical stimulation of an axon can result in an action potential being propagated in both directions along the axon, one direction towards the soma and another toward the distal portions of the neuron. In situations in which an action potential initiated in an axon invades a soma, the electrophysiological state of the soma can be changed. If a soma becomes depolarized, less dendritic stimulus maybe required to initiate an action potential, and the nerve can be stimulated relatively more easily. Conversely, if the soma becomes hyperpolarized, then it can become less sensitive to stimulation and can be inhibited.

Once an action potential has occurred, many neurons become unable to generate an action potential for a period thereafter ("refractory period"). During the refractory period, the nerve may not respond to stimulation.

The multiplicity of nerve types, neurotransmitter types, and receptor types and the differing effects of activating those receptors can have implications in health and disease. Thus, unbalanced or unopposed action by any of the above-described nerve, neurotransmitter, or receptor types may lead to specific disorders. For example, causes of migraine headaches include unopposed vasodilation of certain blood vessels which can lead to increased pressure on sensitive nerves, leading to painful sensations. Conversely, unopposed vasoconstriction can lead to decreased perfusion, local acidosis, and pain associated with acidosis. If the vasoconstriction is sufficiently sever, loss of tissue function can occur. In certain cases, decreased perfusion of a portion of the central nervous system can lead to strokes or other dysfunctions.

Many tissues and organs can be influenced by multiple nerve types described above. Thus, certain tissues, such as voluntary muscle can have somatic nerves that innervate muscle fibers, and the blood vessels within the muscle can be influenced by autonomic sensory and/or motor nerves. Thus, an organ or tissue can be influenced by multiple types of nerves, neurotransmitters, and transmitter receptors. In certain situations, different nerves, transmitters, and/or receptors can counteract the effects of others, resulting in inhibition of nervous function, whereas in other situations, one mechanism can increase the function of another, resulting in activation. Therefore, improper balance between different inhibitory and stimulatory mechanisms, can, according to one hypothesis, lead to symptoms and disease.

H Nerve-Nerve Interaction

In addition to nerves having different effects on end organs, different nerves can have influences on each other. By way of illustration, FIGS. 1a–1d depict two different nerves, called "A" and "B", impinge on another nerve ("C"). In FIG. 1a, nerves A and B each affect nerve C. Nerve A releases a transmitter that stimulates (+) nerve C, and nerve B releases a transmitter that inhibits (–) nerve C. Activation of nerve A by itself, can lead to activation of nerve C. Activation of nerve B by itself does not activate nerve C. However, stimulation of nerves A and B together may result in either activation or no activation, depending on the relative efficacy of nerves A and B on nerve C.

Figure 1B:
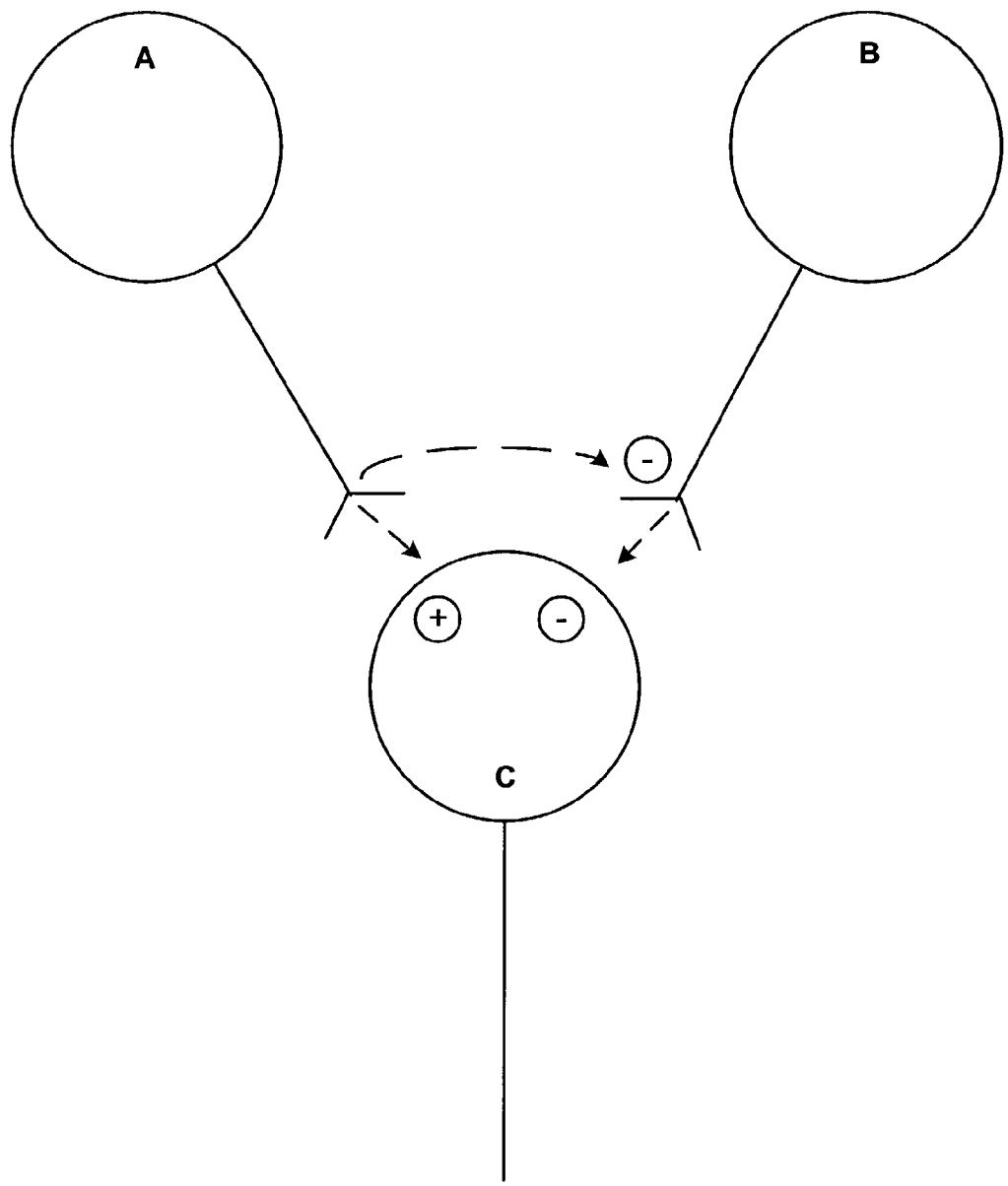
Figure 1C:
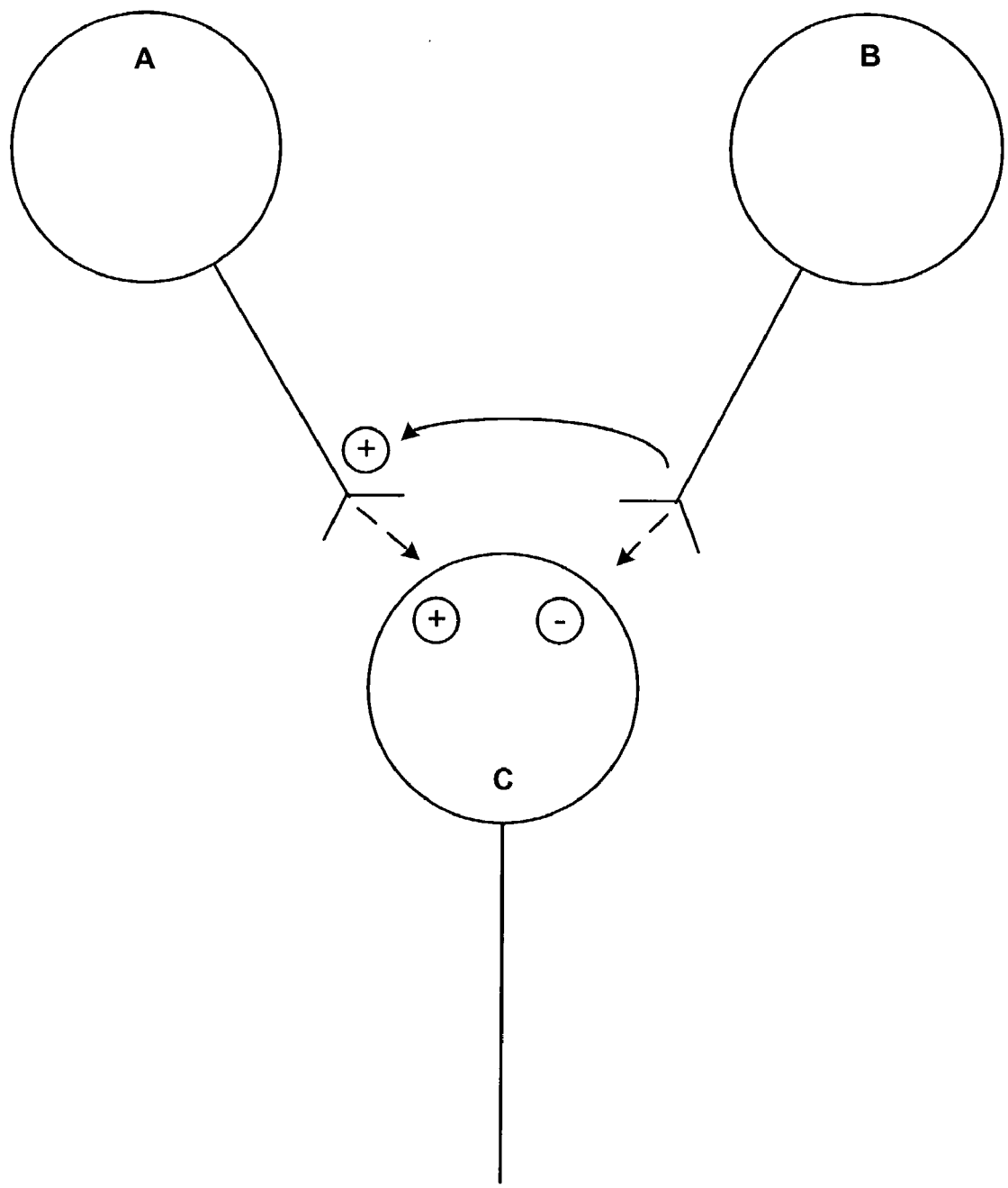
Figure 1D:
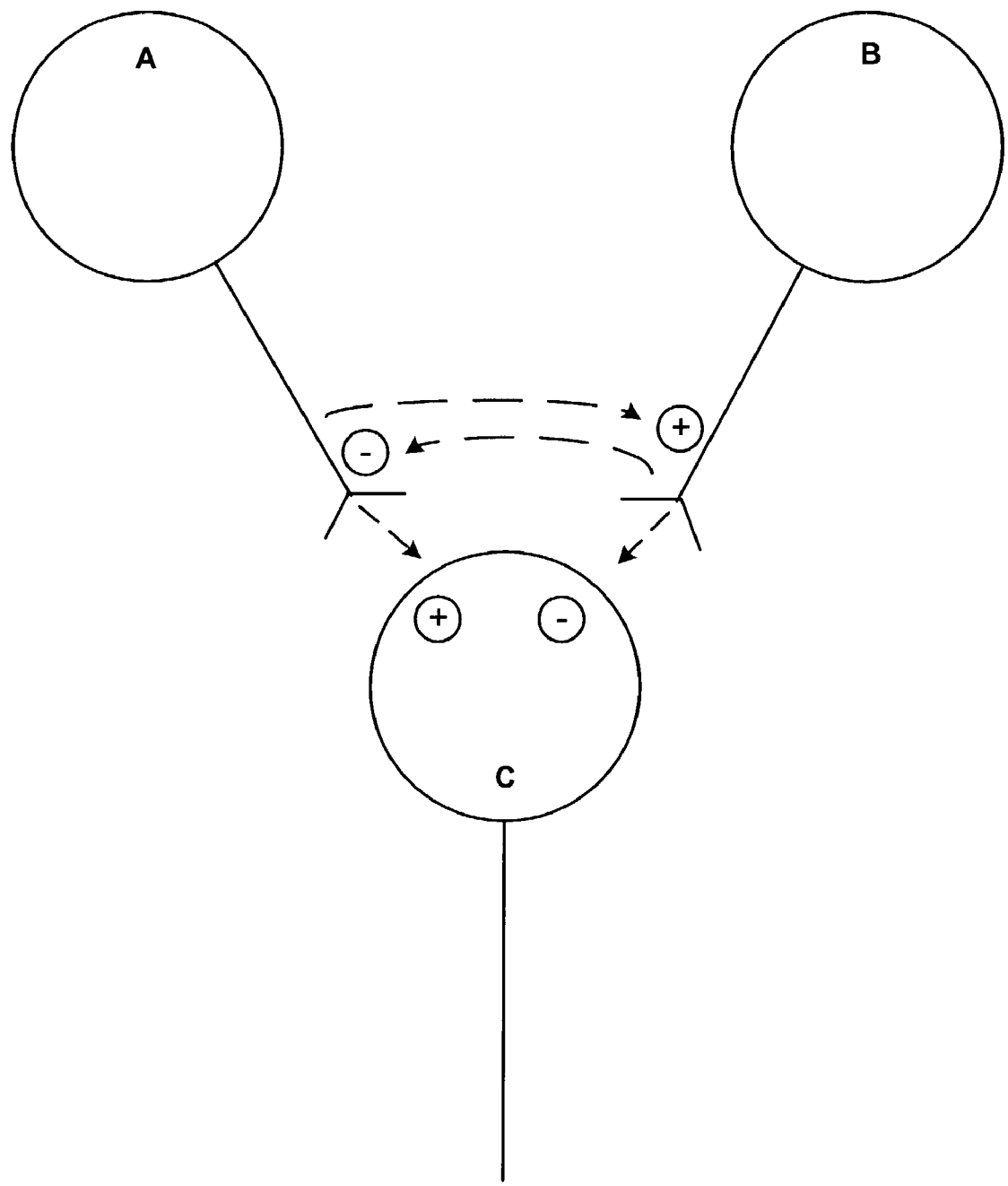

FIG. 1b depicts a situation in which the neurotransmitter for nerve A can stimulate nerve C and can inhibit the release of transmitter from nerve B. In this situation, activation of nerves A and B can result in activation of nerve C. FIG. 1c depicts a situation in which the transmitter of nerve B stimulates the release of transmitter from nerve A. Thus, activation of nerves A and B together can result in more of the transmitter being released from nerve A than can be released in response to stimulation of nerve A alone. FIG. 1d depicts a situation in which nerve A stimulates release of transmitter from nerve B, and nerve B inhibits release of transmitter from nerve A. Activation of nerve A promotes the release of transmitter from nerve B, which inhibits transmitter release from nerve A. Thus, activation of both nerves A and B will result in a predominant effect of nerve B, because release of transmitter from nerve A will be inhibited. The net effect will be an inhibition of nerve C.

Figure 1E:
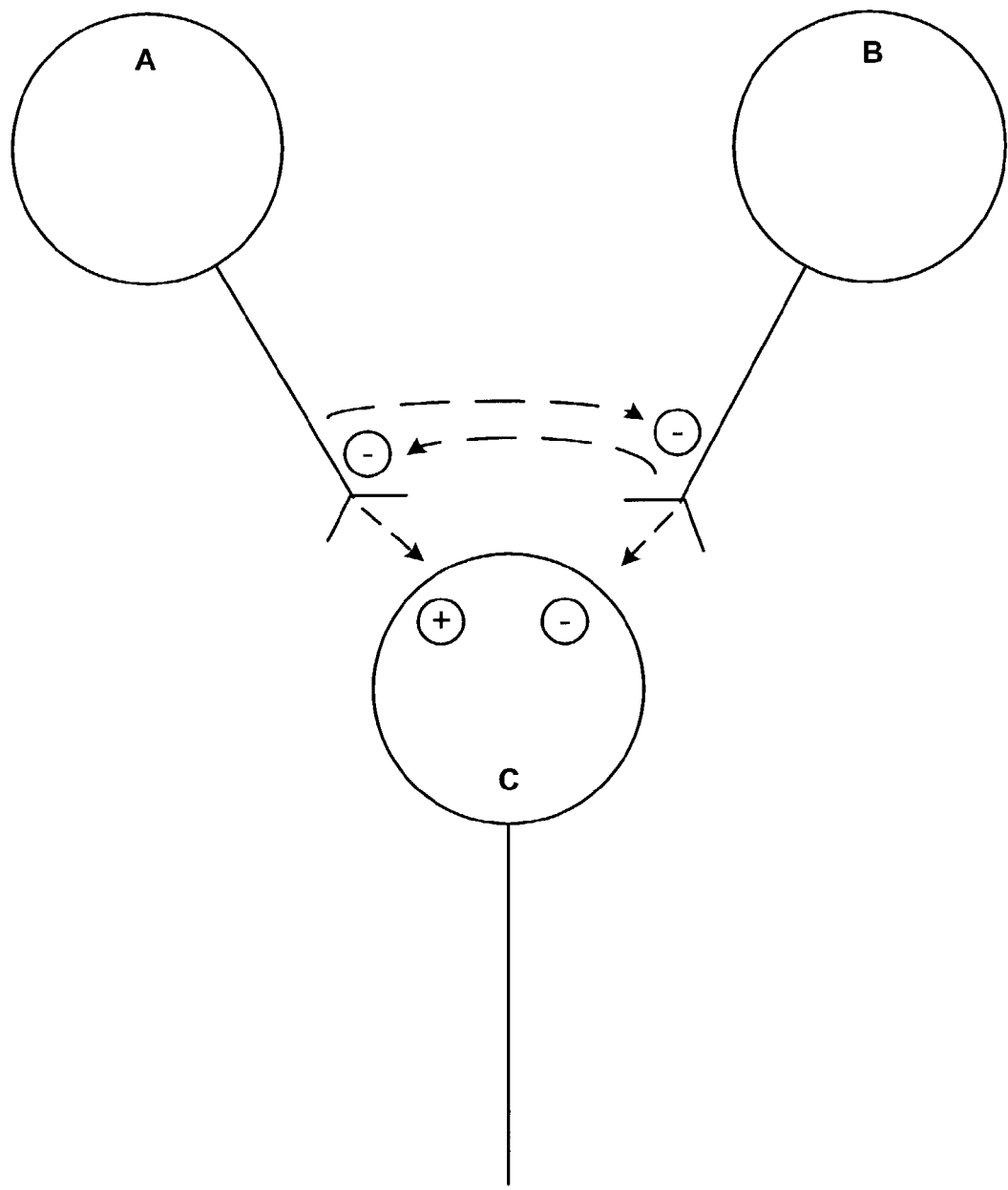

FIG. 1e depicts a situation in which nerves A and B each inhibit transmitter release from the other. If nerve A is activated, it will inhibit the actions of nerve B, and if nerve B is activated, it will inhibit the actions of nerve A. If one nerve is activated more than the other, that effect on nerve C will be more pronounced. Simultaneous activation of both nerves A and B will result in an outcome that depends upon the relative potencies of effects of transmitters on the nerves and on nerve C. This type of mutual inhibition typically characterizes mechanisms that promote steady-states and relatively low amounts of transmitters being released.

For example, under certain situations, acetylcholine can act on adrenergic nerves to decrease the release of adrenergic neurotransmitters such as norepinephrine. Conversely, under certain circumstances, norepinephrine released by adrenergic nerves can decrease the release of acetylcholine from cholinergic nerves. If there is a high level of activation of, for example, the adrenergic systems, then increasing the level of cholinergic activity may tend to decrease the effects of the adrenergic stimulation. Similarly, if there is a high level of activation of the cholinergic systems, increasing adrenergic activity may decrease the effects of the cholinergic stimulation.

Figure 1F:
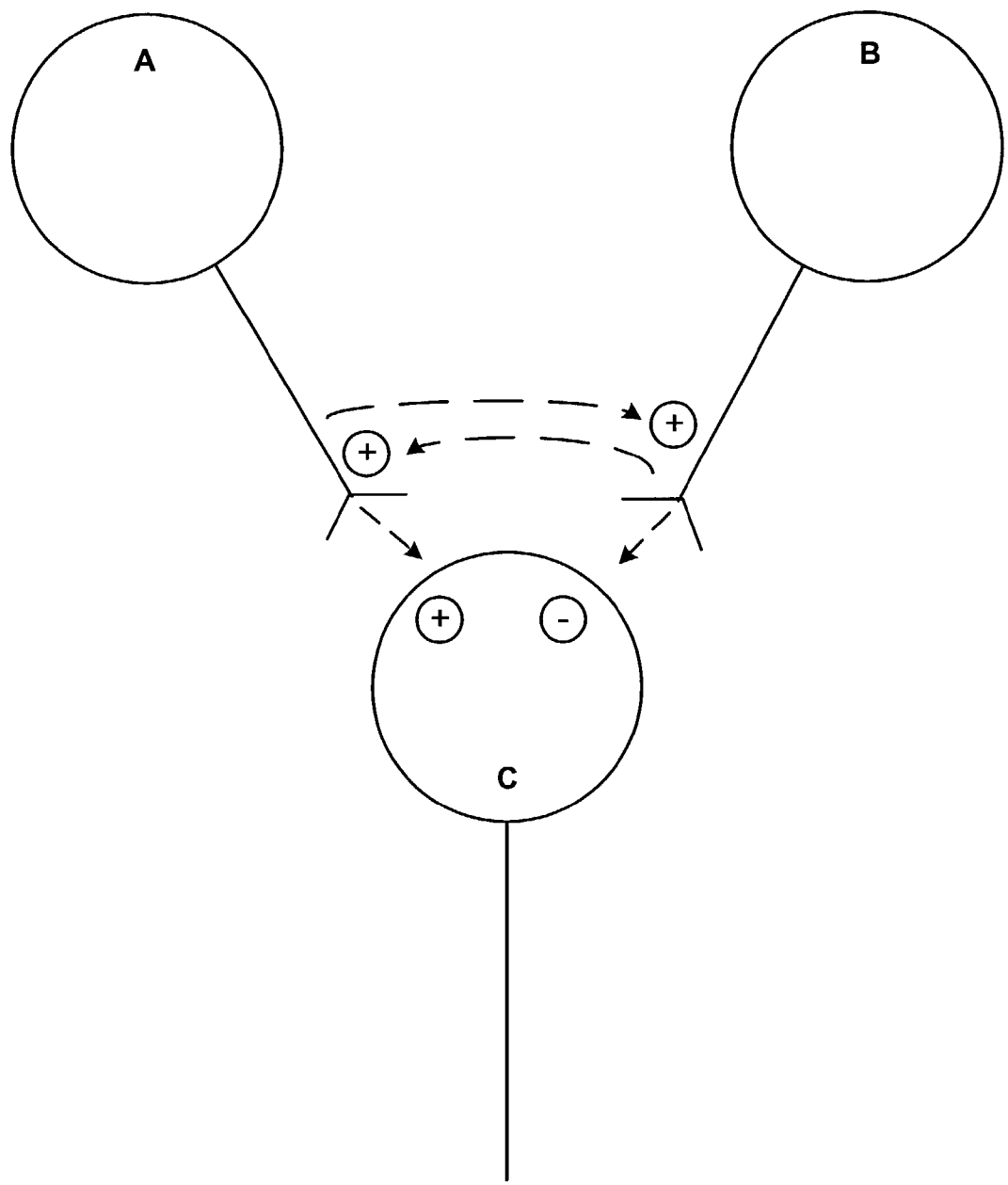

FIG. 1f depicts a situation in which the neurotransmitters of both nerves A and B increase the release of another transmitter from the other nerve. In these situations, the effect on nerve C will be difficult to predict, as the effect will depend on the magnitudes of the interaction and on the effects of each transmitter on nerve C. Moreover, relationships such as these can also result in the depletion of transmitters from nerves A and B, decreasing their ability to respond to stimuli.

These types of nerve-nerve (or "neural") interactions can occur at the level of the end organ, at the ganglion level, at the spinal cord level, at the medullary level, or any other location at which different types of nerves can interact with each other. Abnormal potentiation and/or inhibition of one or more of these levels of the nervous system can lead to disorders. Although the exact mechanisms may be difficult to predict in advance, the methods of this invention can permit a phenomenological approach to therapy, the efficacy of which can be evaluated separately from any particular mechanism of action. By focusing on physiological responses of treated organisms, organs, tissues and cells, the practitioner can determine the optimum therapeutic approach and can achieve desirable results, regardless of the exact mechanisms of action of electromagnetic radiation.

III Therapeutic Goals

Thus, a therapeutic goal of certain methods of this invention is the restoration of proper "balance" between different regulatory mechanisms responsible for the disorder. Accordingly, one hypothesis to account for the beneficial effects of the methods of this invention is that by returning proper balance between the different branches of the autonomic or somatic nervous systems and the tissues innervated, adverse symptoms can be alleviated. For example, in adrenergic or sympathetic overactivity, reducing the activity or "tone" of the sympathetic nerves can be beneficial. Similarly, in systems in which both parasympathetic and sympathetic innervation is important, sympathetic overactivity can be treated by either decreasing sympathetic tone or by increasing cholinergic tone. In systems in which adrenergic, cholinergic, peptidergic, serotonergic, dopaminergic, and other nervous mechanisms are present, complex interactions between the different mechanisms can be a delicate balance, a balance that can be easily upset, causing disorders. Thus, according to this hypothesis, one therapeutic aim of the methods of the present invention is the return of the various branches of the nervous system to balance.

According to another hypothesis, abnormalities in vascular perfusion can lead to disorders and symptoms. For those conditions, vascular hyperperfusion can lead to increased temperature, and hypoperfusion can lead to decreased temperature. Thus, in those conditions, a therapeutic aim is the normalization of blood flow. For disorders characterized by hyperperfusion, therapeutic aims include decreasing blood flow, and for disorders characterized by hypoperfusion, therapeutic aims include increasing blood flow.

The above hypotheses represent only possible mechanisms of action of the methods of this invention. Other mechanisms may be responsible for the beneficial effects of electromagnetic radiation therapy, and we do not intend to limit the scope of this invention to any particular theory or theories of operability.

Evaluation of the efficacy of therapy with electromagnetic radiation may involve impressions of the patient, including the degree of the symptom experienced, or may be evaluated using one or more of a variety of methods described below.

IV Methods for Treating Specific Disorders

To treat disorders using the methods of this invention, one can vary wavelength, bandpass, duration, intensity, pulse frequency, or time-dependent changes one or more of these variables to achieve beneficial results. One beneficial purpose of using variations of the above characteristics over time is to accommodate differences in individual subjects' responses to different stimuli. Thus, in a situation in which a subject does not respond to "pure" light having a fixed characteristic, the use of variable characteristics can provide a desirable level of activation or inhibition of the affected portion of the subject's body, thereby increasing the efficacy of treatment and increasing the numbers of subjects that can benefit from treatment.

Headaches and Stroke

Certain aspects of this invention involves treating disorders of the nervous system. In certain embodiments, patients suffering from headaches or strokes can be treated by exposing the occipital nerve. The occipital nerve exits the base of the skull at the cervical-1 ("C-1") location. Stimulation is desirably near a midpoint between the spinous process and the mastoid region. This region may be identical to the acupuncture point GB 20. This area is usually tender to palpation, as can be the area of the frontalis muscle. Hyperactivity of the frontalis muscle can be a significant cause of headaches. Treatment of the GB 20 region can be especially useful of GB 20 or the frontalis muscle is unusually tender to palpation.

Efficacy of treatment can be assessed by surface electromyography ("sEMG"), which monitors the electrical activity of the structures (e.g., muscles and nerves) beneath the skin at that location. In frontalis muscle hyperactivity, the increased muscular contractions can be detected as increased frequency and amplitude of electrical potentials monitored over those locations.

In many patients, application of pressure to GB 20 can produce pain radiating from the sub-occipital region, in the transverse hemicranius pathway, over the top of the head, and terminating at the inner canthus of the eye, typically at or below the level of the eyebrow. A portion of the nerve exits the scull at that location from a small fossa that can be identified by palpation. Thus, electromagnetic radiation therapy of that point, using any wavelength between about 200 nm and about 1600 nm can be useful, as well as at GB 20 can decrease the muscle hyperactivity that causes the headache pain. Radiation in the orange range of the visible spectrum can be used at the start of therapy. Alternatively, yellow radiation can be used. In certain embodiments, mixtures of orange and yellow light can provide improved therapeutic efficacy. However, other wavelength ranges can also be beneficial, including those in the infrared range.

In certain of these embodiments, it can be desirable to provide electromagnetic radiation at a specific angle relative to the patient's head. By applying the beam of radiation at an angle of about 45° cephalad, the total time required to treat symptoms can be substantially decreased. Applying electromagnetic radiation at both sites for a duration of about one (1) minute can result in improvement in symptoms, including increased muscle relaxation, increased sense of being at ease and reduction in pain. Additionally, in untreated patients, palpation of the temporal artery can result in significant discomfort, and with treatment, the sensitivity of the temporalis artery can be significantly decreased.

In certain embodiments, it can be desirable to use two separated, distinct frequencies within the electromagnetic spectrum. In these embodiments, one may expose a proximal portion of a nerve and a distal portion of the same nerve to radiation of different wavelengths. In some embodiments, it can be desirable to vary the wavelength of the electromagnetic radiation during therapy. Thus, one can initiate therapy using radiation of one wavelength, and then progressively alter the wavelength. For example, in situations in which "relaxation" of a nerve is desired, one can use radiation in the orange. As therapy progresses, one can shift the wavelength to shorter wavelengths, such as yellow, which can provide a "stimulation" of the nerve. Alternatively, one can use multiple wavelengths simultaneously, with the ratio of each being selected. For example, one can use orange:yellow wavelengths in a ratio of about 30:40, to achieve a desired balance between "relaxation" and "stimulation" of the nerve. However, it can be appreciated that other ratios of colors may be useful.

Inhibition of Hyperactive Nerves: Neuronal Pain

In situations in which nerve "hyperactivity" is a source of symptoms, it can be desirable to expose that nerve to electromagnetic radiation having wavelengths in the blue region of the visible spectrum. Additionally, it can be desirable to provide pulse rates in a range of about 1 Hertz (Hz) to about 1000 Hz. In addition, in certain embodiments, it can be desirable to expose the nerves on the contralateral side of the body. It can be desirable to stimulate the site of pain, or more proximally along the distribution of the nerve, or alternatively, more distally.

In situations in which the pain is not responsive to localized treatment, it can be desirable to apply radiation at the coccyx, the lower end of the spinal column, and another beam of radiation to the top of the spinal column, for example at or near C1. In some patients with this type of disorder, thermography can show a region of elevated temperatures, termed a "hyperthermic stripe" along the axis of the spinal column. Exposing the two ends of the spinal column to electromagnetic radiation can result in decreased temperature of the hyperthermic stripe and can decrease the pain. It can also be desirable to apply therapy using small, discrete locations, with narrow beam radiation to treat nerves. Alternatively, to treat muscles, it can be desirable to use radiation having wider dimensions to treat a wider area of the muscle.

Treatment of Myofascial Syndrome

Myofascial syndrome is characterized by specific areas of their musculoskeletal system that are particularly painful. Many cases of myofascial syndrome arise from whiplash, automobile injuries, falls, skiing accidents, stress trauma, and repetitive stress injuries. In many patients having myofascial syndrome, usual allopathic prescriptives, including ibuprofin and muscle relaxants have been unsuccessful at alleviating symptoms. In some patients, antidepressants have also been found to be unsatisfactory. Physical therapy including massage and stretching have also been found to be unsatisfactory. In some cases, electrical stimulation therapy has been used, and in some cases, found to be unsatisfactory. Additionally, exercise rehabilitation can make symptoms worse.

One hypothesis to account for myofascial syndrome includes muscle hyperactivity. With repeated use, the muscles become contracted and painful. Limited motion can place additional stress on the tightened musculature and the spinal column, and pain can be found between the shoulder blades (scapulae), neck, radiating from the head, or pain in the lower back.

Physical examination can reveal taught musculature, either focally or regionally, and deep palpation results in tenderness. Some of these patients have limited range of voluntary motion, but passive motion is unhindered. Typically, these patients have no geigenhaulten patterning and no end point rigidities.

Thermal imaging reveals elevated temperatures in specific regions located above or near a trigger point. In the upper body area, such as the upper back, these points can be located at the mid portion of the upper trapezius, the levator scapula and the rhomboid grouping. In some patients, the hyperthermia is unilateral, but in certain of these cases, the upper trapezius on the right and the levator scapula on the left will be involved.

Therapy for these patients is generally to expose the affected muscles to electromagnetic radiation beginning at the muscle's origins and then progressing to the muscle's insertions. The specific sites to be treated are identified by palpitation, with the trigger points being those most sensitive to palpation and result in referred pain.

The wavelengths of radiation include orange first to alleviate the pain. Next, radiation in the blue range is useful, and in certain circumstances, purple radiation is desirable. Radiation in the shorter visible range (blue and purple) can result in cooling an area. In pain associated with hyperthermia, cooling can be associated with reduction in pain.

EXAMPLE 1

Treatment of a Patient Having Myofascial Syndrome and Right Lower Extremity Pain A patient presented for treatment with a history of right sided, lower extremity pain. Previously, the patient had visited 16 physicians and had undergone a surgical procedure in her neck in an attempt to alleviate the pain. The pain was focused on the right iliac crest region and at the intersection between the buttock and the hamstring muscle grouping. The pain radiated in a course more laterally and then down along the leg, transecting the knee and down the anterior aspect of the leg to the dorsum of the foot. The patient kept her right foot in external rotation. She also had right iliac crest elevation. Her gait had a lateral lurch, in which she shifted her weight to her left leg and attempted to elevate her right leg rather than allow it to move directly forward.

Thermography indicated a large area (about 4 inches in diameter) of hyperthermia located over the right gluteus medius and minimus musculature. Upon palpation with light digital compression resulted in immediate replication of the pain symptom complex. A diagnosis was made of myofasciatis with a trigger point with a zone of referred pain.

Application of electromagnetic radiation in the infrared wavelength range resulted in substantial alleviation of pain and her gait became normal. With three additional treatments, one per day, the patient was discharged in an asymptomatic state.

Treatment of Sympathetic Hyperactivity

Certain patients present with easily fatigued muscles. In certain of these patients, one underlying cause can be associated with hyperactivity of the sympathetic nerves innervating the blood vessels in the muscle. If the sympathetic nerves are hyperactive, the blood vessels can be in a state of heightened contraction, resulting in decreased perfusion of the muscle. With decreased perfusion, there can be a lowered supply of nutrients and oxygen, and a concomitant increase in lactic acid and carbon dioxide in the muscle, leading to acidosis. These conditions can contribute to muscle fatigue. Upon exertion, the patient can experience a burning sensation, which, in time can lead to dysfunction.

Thermography of these areas typically can show areas of lower temperature, in contrast to the areas of hyperthermia associated with myofascial syndrome. Electromagnetic radiation therapy of the muscles can lead to further decreases in observed temperature, and may not relieve symptoms.

In these patients, it can be desirable to treat the blood vessels leading to the muscle, and not to directly treat the muscle. Thus, one approach to treat lower extremity sympathetic hyperactivity is to expose the abdominal aorta to electromagnetic radiation. In general, the sympathetic innervation of a peripheral blood vessel, such as a leg artery, follows the path of the blood vessel to that site. Thus, because the arteries of the legs arise from the abdominal aorta, exposing the abdominal aorta to radiation can affect more peripheral sites along the blood vessel's distribution, in a fashion in some ways similar to that of the affects of exposing proximal nerves can affect more distal portions of the nerve.

One method of treating such patients is to expose an area of the abdominal aorta at a location where tissues overlying the abdominal aorta are relatively thin. Two such areas include one near the umbilicus, and another is immediately below the xyphoid process, the lower part of the sternum. Effects of exposure of the abdominal aorta can be monitored by thermography of the affected area of the limb, by temperature strips, temperature sensors, or by Doppler blood flow measurements. If the thermal image of the affected area, such as the plantar portion of the foot, shows increased temperature with treatment, pain can be alleviated. In those patients for whom this approach does not provide sufficient relief, one can expose an area of the femoral artery. The femoral artery is relatively superficial in the groin area. Identification of a site of exposure can be accomplished by palpation of the arterial pulse at those locations. Additionally, in some patients, exposure of the popliteal artery can provide relief. In some embodiments, it can be desirable to treat the popliteal artery within the popliteal fossa.

In a minority of cases, the above methods may not provide sufficient relief. In these situations, it can be desirable to expose the saphenous vein, from distal to proximal, with electromagnetic radiation. In some of these cases, such "painting" techniques can result in increased perfusion to the affected location, and reduction in pain. Although the mechanism for this effect are uncertain, one possibility is that electromagnetic radiation results in contraction of the veins, thereby increasing venous return. Moreover, stimulation of autonomic nerves in the veins may result in activation of autonomic nerves in the arteries leading to that site.

Treatment of Temporomandibular Joint Syndrome

Temporomandibular joint syndrome ("TMJ") is a condition characterized by complaints of clicking of the jaw upon opening ("crepitance"), and localized pain and pain radiating into the head, neck and upper back area. In some patients, the radiation proceeds towards the frontal, the area of the face, down the jaw and into the mouth region. In many patients, headaches are common, and in some cases can be severe. Upon palpation, the masseter muscles can be in spasm, along with the temporalis and buccinator groups. Thermography can reveal circumscribed regions of hyperthermia located toward the anterior aspect of the jaw. Superficial EMG measurements can be used to directly assess muscular activity. Latent myospasm can be detected in certain patients upon slowly opening and closing the jaws, by rotating the jaw by translating the jaw forwards and backwards, or other motion. If motion is limited, is not smooth, or is asymmetrical, the muscles responsible for the limited motion will be targets for therapy.

Electromagnetic radiation therapy for patients with hyperthermia can include a 1–2 minute period of exposure to a beam of radiation in the orange or yellow wavelengths, followed by wavelengths in the blue region of the spectrum. In situations in which the symptoms are associated with hyperthermia, blue radiation can be desirably used. In situations in which the affected area is cool or cold by comparison to normal sites, it can be desirable to treat with longer wavelengths, in the infrared/red/scarlet/orange wavelength ranges to increase the temperature (and blood flow) to those sites. In those patients with crepitance, it can be desirable to expose the inner aspects of the mouth with radiation at sites over the affected muscles. Using devices as described in U.S. Provisional Patent Application titled: "Dual Wavelength Fiber Optic Illuminator", Allan Gardiner, inventor, filed concurrently, herein incorporated fully by reference, simultaneous illumination of inner aspects and outer aspects of the muscles is possible and can be beneficial. In some embodiments, it can be useful to apply radiation to the origins and insertions of the muscles. In other embodiments, it can be desirable to illuminate the belly of the muscle. Subsequently, if desired, one can have the patient close the mouth and exert some compressive force to hold the jaws in a closed position. With the muscles under tension, treatment can be applied. If desired, one can treat both sides of the jaw. In some cases, treatment of the contralateral side can provide greater relief than unilateral treatment. Subsequent palpation, and observation of the patient's jaw motion can reveal which muscles and muscle groups are still holding tension.

In many of these patients, it can be desirable to take an incremental approach, first identifying a significantly spastic muscle and treating that one first. Then, other areas may become apparent as sites of spasm. Either simultaneously with or subsequent to treatment of spastic jaw muscles, the sites of referred pain or trigger points can be treated to provide additional relief. In cases where the site of referred pain is covered by hair, electromagnetic therapy can be applied through the hair.

In certain patients, it may be difficult to make a differential diagnosis of referred pain with myospasm from myositis. The symptoms may be nearly the same, and the physical examination may be the same. However, monitoring temperature may yield different results, with areas having myospasm showing cooler temperatures and myositis showing warmer temperatures than the surrounding normal sites. Because of the differences in temperatures, different therapeutic approaches can be indicated. Myospasm can be advantageously treated with long wavelength radiation, such as infrared, red, scarlet, and orange, whereas myositis can be advantageously treated with shorter wavelength radiation, such as blue.

Trigeminal Neuralgia

Trigeminal neuralgia ("TN") is a condition characterized by pain of the face associated with the distribution of the trigeminal nerve. The pain can be associated with a region of hyperthermia located near the ear area, and is usually specific and circumscribed. In certain other cases, of long duration, there can also be an area of hyperthermia immediately behind the mastoid region at the base of the skull and the C1 area. In mild or short-duration cases, the area of hyperthermia is anterior to the ear and the facial aspect is cool.

In these patients, a therapeutic end point can be equalization of temperature distribution. Areas that are warmer can be cooled, by way of example, by using short wavelength radiation. In contrast, cool areas can be warmed using longer wavelength radiation, including infrared radiation. In certain embodiments, it can be advantageous to provide oscillating treatment, in which long wavelengths (e.g., red or infrared) are used in one probe and the other of short wavelength (e.g., blue) for about one minute. Then treatment of both sites with yellow radiation for a period of about one minute is provided. Subsequently, one can alternate between the red/blue then yellow regimen until blood flow is normalized.

EXAMPLE 2

Treatment of a Patient Having Trigeminal Neuralgia

A 70 year-old female patient presented with symptoms of pain associated with oral surgery 10 or 15 years before. During surgery, her mouth was maintained in an extended position (wide open) during surgery in which several extractions were performed. She had been on prescription medications for pain for many years, and in spite of the pharmacological treatments, her pain was so severe as to prohibit her from inserting and using her dentures.

In this situation, her trigeminal nerve was treated using infrared radiation as described above, and resulted in alleviation of her pain to the point where she could use her dentures and carry on normal conversation.

Treatment of Post Herpetic Neuralgia

Herpes zoster is thought to be the causative agent of "shingles," a viral disease involving infection of the sensory nerves to the skin, and possibly other organs. In the skin, the virus can cause epithelial infection with blistering and severe pain. The lesions typically will heal, but persistent, post-herpetic pain can be long-lasting and severe.

Diagnosis of post-herpetic neuralgia can be made by history, physical examination (presence of scarring) and/or by thermography. Post-herpetic neuralgia can be associated with heightened sensitivity to touch, and in some cases, even very mild physical stimulation (such as that associated with blankets) can cause severe pain. Thermography can reveal a pattern of hypothermia in the intra-rib area, which can continue, in a horizontal pattern from posterior to anterior. In certain situations, in which a particular nerve is involved, one can observe an oval region of hyperthermia.

Treatment of post-herpetic neuralgia can be bilateral, involving a 2-minute exposure to infrared radiation, with one beam directed toward the posterior exit of the rib, and the other at the anterior termination of the rib. This regimen can be associated with decreases in the characteristic deep, searing pain, which can be replaced with a superficial pain that can be considered to be tolerable by many patients. In certain embodiments, it can be desirable to treat regions of referred pain, for example in nearby ribs. Therapy is repeated at intervals, with a period of about 3 days between treatments, then progressing to intervals of about 1 week, and then 2 weeks apart. After about 6–10 weeks of such a therapeutic regimen, substantial recovery can be observed. Thus, electromagnetic therapy can be effective in many patients with pain of long duration. In addition to Herpes zoster, post-herpetic neuralgia associated with Herpes simplex can be effectively treated using electromagnetic radiation therapy of this invention. Herpes simplex is a virus that, according to some, can reside in dorsal root ganglion cells for long periods of time. Characteristic symptoms include hypersensitivity to pressure and localized swelling, or edema, can be present. An additional manifestation in the trigeminal nerve, which innervates portions of the head and face, can include cold sores. Occasionally, the virus can be activated and transported down the sensory nerve to the skin, where a herpetic outbreak can occur. As with neuralgia associated with Herpes zoster, a major symptom can be deep, searing pain.

Therapy of post-herpetic neuralgia associated with Herpes simplex can involve short wavelength radiation, such as turquoise. In certain embodiments, the treatment with turquoise light (about 500 nm) can be followed by red radiation. It can be desirable to also use vitamin A (100,000 Units), vitamin C and zinc (100 milligrams "mg"). Additional adjunct therapies include elimination of the amino acid arginine from the diet. Nuts, and especially peanuts have large amounts of arginine. In contrast, it can be useful to include additional lysine in the diet. It can be especially desirable to begin electromagnetic radiation therapy as soon as symptoms begin, even before herpetic eruptions are apparent. In certain cases, treatment at a frequency of about twice per day can be effective at decreasing the severity of a herpetic outbreak, and in some cases can prevent further progression.

Gangrene

Gangrene is a severe condition in which tissues die as a result of inadequate nutrition and/or oxygenation. Gangrene can be caused by trauma, by frostbite, by infection, or by certain metabolic disorders. Once a tissue's nutritional state is sufficiently compromised, infection can set in, causing further destruction of healthy tissue, and leading to increased morbidity. Although there may be many causes of gangrene, a common feature can be decreased vascular perfusion to the affected area. Although the causes of decreased perfusion are not known for all gangrenous conditions, overactivity of vasoconstriction may play a role in one or more types of gangrene.

Thus, one therapeutic aim in treating gangrene is to increase vascular perfusion, thereby returning the affected tissue to a more normal nutritional state. Therapy using electromagnetic radiation can be effective in improving the effects of gangrene, and can also help slow the progressive destruction of tissues that characterize the disorder. In general, it can be desirable to provide some sterilizing radiation, in the form of ultraviolet radiation. Ultraviolet radiation is known to be antibacterial, and when used in conjunction with radiation wavelengths that promote increased perfusion, can be effective in alleviating gangrenous symptoms and findings.

EXAMPLE 3

Treatment of Gangrene

Skin lesions associated with gangrene can be treated using electromagnetic radiation therapy with low frequency ultraviolet radiation. In a patient with gangrene of the legs, electromagnetic radiation of infrared wavelengths was used, first at a point, identified as kidney-1. Thereafter, additional points were treated and included electrodiagnostic points of the common peroneal, deep peroneal and posterior tibial nerves. Subsequently, infrared radiation was used to "paint" the gangrenous area directly. The patient exhibited improvement in symptoms and mobility.

Diabetic Neuropathy

Diabetic neuropathies are a common source of morbidity in diabetes mellitus. Patients typically present with complaints of burning pain and the plantar aspects of the feet with a decrease in sensory nerve sensitivity. In some patients, the sensory deficit is so severe as to make it difficult for patients to determine whether they are on a carpeted or uncarpeted floor. In some cases, patients find it very difficult to determine whether their shoes are too tight. In certain cases, the symptoms become worse upon lying down.

Thermography reveals bilateral decreased peripheral perfusion and cooling, especially on the plantar aspects of the feet. Additionally, the distal portions of the toes can be cool.

Many patients with diabetes are treated allopathically with insulin, neurontin, anti-anxiety medications and/or other regimens of pharmaceutical agents and diet. Therapeutic goals include increasing peripheral perfusion. In certain embodiments, in situations in which allopathic remedies are less than completely effective, treatment can begin by exposing the common peroneal, deep peroneal, posterior tibial and sensory nerves with infrared radiation to "balance" the innervation of the affected site. Then, radiation in the purple wavelength range can be used. Then the wavelength can be changed to yellow, to "stimulate" the nerves, and in certain embodiments in which the neuropathy is of long duration, to green and then to yellow. After a course of electromagnetic radiation therapy is completed, it can be desirable for the patient to be reevaluated by an allopathic physician to appropriately readjust the prescriptive medications.

EXAMPLE 4

Treatment of a Patient with Diabetic Neuropathy

A man presented with a history of diabetes who was unable to walk distances greater than about 3 feet. Allopathetic remedies were ineffective. He could only sleep after plunging both feet into ice water to numb them. He was unemployable and 100% disabled.

After 120 days of management using infrared electromagnetic radiation therapy of this invention using infrared radiation, he obtained a position that involved walking 3–5 miles per day wearing steel-toed shoes. He has retained that position for 5 years.

Sympathetic Atonia

Sympathetic Atonia ("SA") is a condition associated with complex regional pain syndrome ("CRPS") and Reflex Sympathetic Dystrophy ("RSD"). Complex regional pain syndrome and RSD include characteristic symptoms of coldness in the extremities, coupled with lancinating pain, burning pain and dysfunction. These conditions are typically recalcitrant to conventional allopathic management. Numerous nerve blocks, high doses of prescriptive medications and surgical intervention may not be able to control this highly unique and individualized disorder. In many cases, the diagnosis of CRPS and RSD carry a high level of permanent impairment.

In many of the above type of disorders, a therapeutic goal is to increase perfusion of the affected region. In certain embodiments, it can therefore be desirable to use infrared, red, or orange wavelengths of electromagnetic radiation.

In certain patients having similar symptoms, the extremities are warm and not cold, resulting in a variant of RSD known as "hot RSD". These patients are characteristically unresponsive to conventional allopathic management and electromagnetic radiation therapy using infrared/red wavelengths was ineffective.

To treat patients having hot RSD, initial sensitivity testing can include exposing the symptomatic extremity using wavelengths of radiation in the blue spectrum. The therapeutic goal can include first, producing normal temperatures ("euthermia") or even hyperthermia. Then, one can provide radiation in the scarlet portion of the spectrum to the contralateral side. Then, infrared radiation can be used to sweep the contralateral inferior cervical ganglion innervating the upper extremity, or the femoral artery and the sacrococcygeal junction for treating lower extremities.

The duration of therapy for CRPS, RDS or hot RDS can be selected based on observations of the appropriate extremity. Methods that can be especially useful include pulse oximetry or liquid crystal temperature scales or thermography. The initial dose of electromagnetic radiation used can be terminated at a time when an alteration in the monitoring variable is detected. A second series of therapeutic applications can be provided the next day, for example, 24 hours later. Subsequent treatments can be carried out periodically after that time.

Post Surgical Joint Replacement Syndrome

Many patients having joint replacements respond successfully to standard physical therapy measures. However, many develop new symptoms when they begin to discard their ambulatory aids, such as crutches, walkers and the like. Although physical therapy is typically repeated, symptoms may persist with time and new symptoms can appear. New symptoms can include poor lymph drainage ("lymphedema") and pain, either proximal to the replaced joint, distal to the joint, or in both locations. In some cases, the pain can be progressive.

Electromagnetic radiation therapy can be successful in alleviating joint pain and lymphedema, can reduce or eliminate the associated myospasm and/or myositis and can result in increased active range of the affected joint. In certain embodiments, therapy can begin with the practitioner identifying the perfusion of the surgical scar, for example, using thermography, temperature sensors, or temperature scales placed on the skin. If the scar is hypothermic, then radiation in the scarlet wavelength range can be used. In certain of these embodiments, it can be desirable to apply two beams of radiation, one at each end of the surgical scar. In cases in which the scar is hyperthermic, it can be desirable to use wavelengths in the blue range of the spectrum. Palpatory examination performed at the surgical site can determine the presence of absence of myospasms. If myospasm is detected, as reflected by reduced temperature, then radiation in the orange wavelength range can be advantageously used at the trigger point to produce muscle relaxation. If myositis is found, as reflected by hyperthermia, then radiation in the green portion of the spectrum can be used.

Then, the practitioner can establish the nerves that traverse a course through the surgical field, or those which specifically innervate the affected musculature. Dual illuminators can be used with radiation in the yellow wavelength range, with one beam directed at the spinal exit of that nerve and a second beam directed at a superficial cutaneous branch of that nerve. Patient tolerance can be monitored by observing thermal images of sites along the distribution of the affected nerve. When decreases in perfusion, or cooler temperatures, are observed, treatment can be terminated.

Once the desired therapeutic goals have been met, the patient is then placed in a recumbent posture to passively move the affected joint through its range of motion. The practitioner can slowly move the extremity through the pain-free arc of motion and then can gently provide a slight overpressure to extend the range of motion of the affected joint. Any specific abnormal motions are noted, and the patient is then provided instructions for exercises to do to assist in increasing mobility of the affected joints. Treatment can be advantageously repeated daily for three days to provide an objective basis for improvement.

Acupuncture

Electromagnetic radiation therapy can be a method of choice for non-invasive acupuncture. Standard forms of diagnosis can be used (e.g., Akabane, EAV, or electric resistance measurements and the like). The practitioner selects points to be treated and chooses wavelengths that can produce the desired physiologic properties. The beam of radiation can then be selected to have a small diameter, if desired. Monitoring methods may include an audible sound generator to indicated changes in electrical conductivity, or alternatively, direct measurements of electrical resistance can be provided. Observed changes in monitored variables can indicate effects of therapy.

Additionally, a practitioner may select and locate acupoints manually or with a device to monitor electrical resistance ("ohm meter"). In certain embodiments, the points may be treated immediately, or alternatively, may be marked for future treatment. If auriculotherapy is chosen, the practitioner may further decrease the diameter of the beam to a desired size.

Carpal/Tarsal Tunnel Syndromes

Electromagnetic radiation therapy for patients with hyperthermia can include a 1–2 minute period of exposure to a beam of radiation in the orange or yellow wavelengths, followed by wavelengths in the blue region of the spectrum. In situations in which the symptoms are associated with hyperthermia, blue radiation can be desirably used. In situations in which the affected area is cool or cold by comparison to normal sites, it can be desirable to treat with longer wavelengths, in the infrared/red/scarlet/orange wavelength ranges to increase the temperature (and blood flow) to those sites. In those patients with crepitance, it can be desirable to expose the inner aspects of the mouth with radiation at sites over the affected muscles. Using devices as described in U.S. Utility patent application No; 10/180,643 filed Jun. 26, 2003, now U.S. Pat. No; 6,886,964, issued May 3, 2005, entitled; "Illuminator with Filter Array and Badewidth Controller", Allan Gardiner, inventor, herein expressly incorporated fully by reference, simultaneous illumination of inner aspects and outer aspects of the muscles is possible and can be beneficial. In some embodiments, it can be useful to apply radiation to the origins and insertions of the muscles. In other embodiments, it can be desirable to illuminate the belly of the muscle. Subsequently, if desired, one can have the patient close the mouth and exert some compressive force to hold the jaws in a closed position. With the muscles under tension, treatment can be applied. If desired, one can treat both sides of the jaw. In some cases, treatment of the contralateral side can provide greater relief than unilateral treatment. Subsequent palpation, and observation of the patient's jaw motion can reveal which muscles and muscle groups are still holding tension.

After those points are treated, the practitioner can then examine the associated musculature for the presence of trigger points, myospasm and myositis. If myospasms or myositis of found, it can be treated as described above, or alternatively, a painting method can be used. In certain of these embodiments, one beam can be applied to a distal portion of the extremity, while another beam can be at a proximal site along the muscle. It can be desirable to provide the proximal beam with a configuration that produces a rectangular beam to increase the area of exposure. A painting technique can begin with the rectangular beam moved from proximal to distal along the affected region. If myospasm is observed, then the proximal beam can be in the orange portion of the spectrum and the distal beam can be yellow. If myositis is observed, then the proximal beam can be advantageously green and the distal beam can be yellow. Monitoring muscle tone by surface EMG can be useful. A decrease in the amplitude of signals can provide an objective measure of the patient's response to treatment.

Once a desired result is obtained, the region can again be searched for trigger points. If a zone of referred pain is found by direct physical compression, then a dual beam approach can be used. The beams can be pointed directly at each other with the trigger point between. The ends of the devices can be used to gently compress a trigger point therebetween to increase the effectiveness of therapy.

Hyperperfusion

In situations in which an affected site is relatively warmer than surrounding sites, and in which it is desirable to equalize temperature, it can be desirable to use electromagnetic radiation having relatively shorter wavelengths, such as blue. Conversely, in those situations in which an affected site is warmer than the surroundings, and in which it is desirable to equalize temperature, one can use radiation having relatively longer wavelengths, such as infrared, red or orange. Although the mechanisms that underlie the beneficial effects of the radiation therapy of this invention are not known with certainty, one hypothesis is that cool sites may suffer from vasoconstriction and reduced perfusion, and warmer sites may suffer from too much perfusion. Thus, to treat cool regions, radiation is used that promotes increased perfusion, possibly via inhibiting vasoconstriction caused by sympathetic nerve overactivity. To treat hyperthermic regions, radiation can be used that promotes vasoconstriction, possibly via increasing sympathetic nerve constrictive activity.

Entrainment

For disorders of the central nervous system, therapeutic efficacy can be improved by providing multiple sources of stimulation to the body simultaneously. Thus, in certain embodiments, it can be desirable to provide auditory stimulation via earphones at a known frequency. Simultaneously or alternatively, one can provide visual stimulation with light at the same frequency and/or phase relationship as the auditory stimulation. Further, one can use electromagnetic radiation of peripheral sites at the same frequencies and/or phase relationships as the auditory and/or visual stimulation. By providing several modes of input to the central nervous system, the efficacy of electromagnetic radiation therapy can be increased. It can be appreciated that one or more of the alternative modes can be used. Moreover, it can be appreciated that one may stimulate the eyes using unilateral left or right sided light, or bilateral stimulation.

When the central nervous system is involved in symptoms to be treated, electromagnetic radiation therapy as described herein can be administered simultaneously with electromagnetic radiation delivered to the eyes. Delivery of light to the eyes is known as Syntonic therapy. Syntonic radiation can be provided using a device such as a Spectral Illuminator described by Frank Olstowski. The patient looks at the device that emits light having a designated color and pulse frequency. In certain embodiments of this invention, electromagnetic radiation can be applied to the eyes as well as a superficial portion of a nerve of an affected extremity to be treated. It can be desirable to provide Syntonic and electromagnetic radiation in pulses that are synchronized with each other to produce entrainment. Some fibers in the optic nerve travel to the occipital region of the brain and other fibers travel to the reticular activating formation and may influence the pineal, pituitary, hypothalamus and other portions of the central nervous system.

In certain of these embodiments, it can be desirable to control the phase relationships between the stimuli to the eyes and to the peripheral site. Distances between peripheral sites and a site in the CNS can be substantially greater than the distances between the retina and the same site in the CNS. Thus, because of delays in nerve conduction, impulses initiated in a peripheral site may take longer to reach a CNS site than impulses initiated closer to that CNS site. Thus, it can be desirable to provide pulses of electromagnetic radiation to a peripheral site that precede, by a controlled time, the pulse provided to the retina. The control of phase of these pulses can be accomplished using pulse generators coupled to a common timing device. Alternatively, a computer can be used to adjust the relative timing of the pulses.

In other embodiments, it can be desirable to provide pulses that are out of phase by a desired amount. By adjusting the relative timing and duration of pulses delivered, the practitioner can determine optimum therapeutic conditions. In certain embodiments, it can be desirable to limit or stop the effect of entrainment on the central nervous system to avoid adaptive or compensatory abilities of the body to learn and/or anticipate the stimulus. By using randomized variations in wavelength, rate of change of wavelength, changes in location of illumination or other variable, a higher degree of neural stimulatory specificity can be achieved.

Dental Disorders

Frequently, normal healthy teeth begin to loosen within the sockets. Decreased blood flow creating ischemia and its related sequelae can be a direct result of sustained vasospasm. Thermal imaging of the face and jaw reveals regions of temperature asymmetry. The application of electromagnetic radiation can stabilize the tooth and prevent premature extraction. Electromagnetic radiation can be applied with dual probes, one on the lingual border and the other on the facial border of the affected tooth. The frequencies in the red, red-orange, and yellow ranges can be used concurrently. The appropriate artery and nerve are then treated with radiation in the green range. Dual ultraviolet probes can then be applied to the gingival surfaces of the adjacent and affected tooth and can stimulate dermal cell proliferation and aid as an bacterial and viral retardant. As therapy progresses, temperature asymmetry as monitored by thermal imaging decreases.

Patients having to undergo reconstructive surgery from traumatic insult as well as cosmetic procedures frequently develop masticatory disorders. One cause for these disorders is associated with the jaws having been wired closed from weeks to months. Surface EMG is used as well as palpatory evaluation to locate the affected musculature. Following removal of the wires, the mandible may fail to track properly and/or the jaw may be unable to open more than a few millimeters. The application of electromagnetic therapy can relax myospasms, reducing the tissue anoxia, and can improve function. One probe is placed within the oral cavity at the site of greatest tenderness and the second probe placed on the facial surface. One minute of electromagnetic therapy in the orange-yellow wavelength range is applied and palpatory examination is again performed. Treatment can be continued until the desired result is obtained. When the oral cavity is able to be opened sufficiently, the physician can continue the examination to search for latent trigger points that were not accessible with the mouth closed.

It can be appreciated that in addition to the above disorders, numerous disorders involving excitable tissues can be effectively treated using the methods of this invention. Additional disorders include tension headache, sinus headache, vertebrogenic headache, articular dysfunction, complex regional pain syndrome, joint contracture of the fingers or toes, pain associated with intervertebral disk disorders, muscle injuries involving swelling, polyneuropathy, peripheral neuropathies, post surgical pain, post-traumatic sensory nerve dysfunction, spondylosis, pain and swelling associated with traumatic injuries, ands torticollis.

Treatment of Muscular Spasms

Methods of this invention are well suited to treating conditions involving muscular spasms associated with pain. For example, electromagnetic radiation can be applied to various points on the body associated with electrodiagnostic points, acupuncture points, trigger points, meridians or nerve distributions.

FIGS. 2a–2d depict certain sites useful for application of electromagnetic radiation according to this invention for treating head, neck and upper torso neuromuscular conditions. FIG. 2a depicts a right-lateral view of a subject's head and torso. FIG. 2b depicts a left-lateral view of a subject's head and torso. FIG. 2c depicts a front view of a subject's head and torso. FIG. 2d depicts a rear view of a subject's head and torso. Specific points that can be useful for application of electromagnetic radiation (EMR) include those in Table 1 below.

TABLE 1

Sites of Application of Electromagnetic Radiation

| Right Side Point | Left Side Point | Site of Application of EMR |
|---|---|---|
| 1 | 2 | Inferior aspect of the mastoid process |
| 3 | 4 | Midpoint of the sternocleidomastoid muscle |
| 5 | 6 | Lateral base of the neck |
| 7 | 8 | Acromioclavicular joint |
| 9 | 10 | Superior corocoid process |
| 11 | 12 | Midpoint of deltoid muscle |
| 13 | 14 | Supraclavicular fossa |
| 15 | 16 | Inferior to midpoint of clavicle |
| 17 | 18 | Pectoralis major just anterior to axilla |
| 19 | 20 | Just inferior to the inferior nuchal line |
| 21 | 22 | Just lateral to the vertebral prominence |
| 23 | 24 | Supraspinous fossa |
| 25 | 26 | Midpoint to the spine of the Scapula |
| 27 | 28 | Infraspinous fossa |
| 29 | 30 | Medial to the midpoint of the medial border of the scapula |

EXAMPLE 5

Treatment of Trapezius Spasm with Pain

To illustrate methods for treating spasms of the trapezius muscle with associated pain, we studied a series of 25 patients presenting with pain of the upper back or neck. Patients were selected that had persistent pain which was not responsive to conventional therapy. We treated each patient using EMR delivered by fiber optic illuminator described above. The end effectors for each treatment were positioned above the points to be illuminated, but were not in contact with the subject's skin at any time. The patients were not informed of what was being illuminated or the conditions of illumination. We found that illumination of certain points on these patients using electromagnetic radiation can alter muscular activity of affected muscles. These results also indicate that EMR can be effectively monitored using SEMG methods in real time during treatment.

Patient 1

At the time of the study, patient 1 was a 45 year old female with unrelenting left-sided pain at the suboccipital area made worse by movements. She failed to respond positively to repeated courses of chiropractic therapy, physical therapy, exercise, stretching etc. She reported that the pain was made worse by rotating her head and by slow movements. She reported that no significant reduction in pain occurred.

The subject was treated for three sessions under Investigational Review Board (IRB) supervision using electromagnetic radiation in the visible spectrum, from about 400 nm to about 700 nm. Application time at each site was approximately one minute. Five (5) identified locations, wavelengths, and wavelength variation combinations are indicated by the numbers on the graphs of FIGS. 3a and 3b. Two applicators were used at the same time, with conditions and locations of each illuminator end effector shown in Table 2 below.

TABLE 2

Treatment Protocol for Patient 1

| Treatment Time Index* | Treatment Locations** | Conditions of Illumination*** |
|---|---|---|
| 1 | 22 & 24 | 660 nm ± 80 nm, 2 Hz, 50% Duty cycle |
| 2 | 8 & 16 | 520 nm ± 40 nm, constant output |
| 3 | 19 & 20 | End effector 1: 620 nm ± 20 nm, End effector 2, 420 nm ± 20 nm, constant output |
| 4 | 1 & 2 | End effector 1: 660 nm ± 40 nm, End effector 2: 420 nm ± 20 nm, constant output |
| 5 | 7 & 15 | 660 nm ± 40 nm, constant output |

*The number indicates that the illuminator was turned on. The + indicates that the illuminator was turned off.
**Locations described in Table 1 above.
***Data expressed as central wavelength ± wavelength variation, frequency (in Hertz; Hz), and percent of total duty cycle.

Figure 3A:
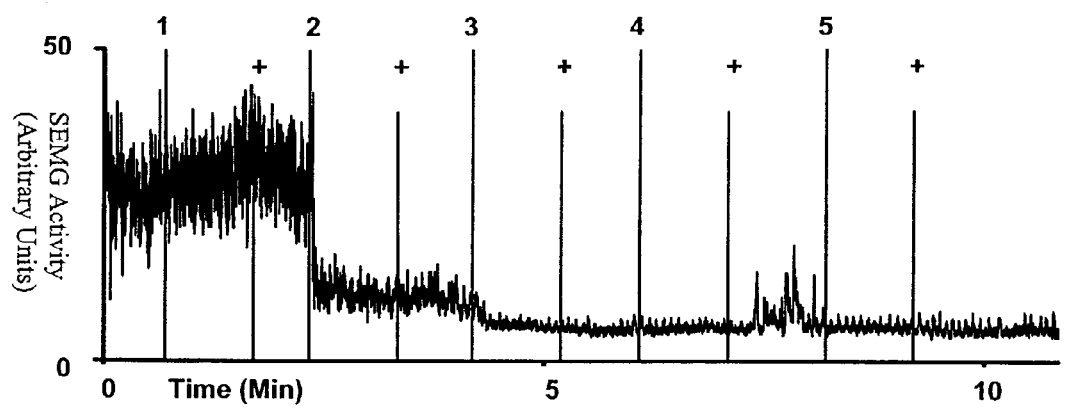
FIGS. 3a and 3b depict surface electromyograms (SEMG) of a subject having trapezius spasm.
Figure 3B:
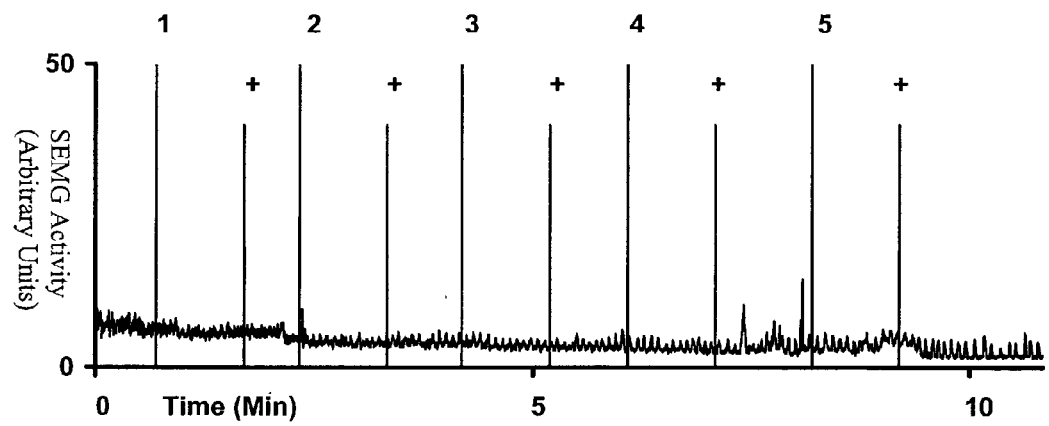

FIG. 3a depicts the SEMG trace of the affected, left side of the subject. During the pre-illumination period, the graphs shows relatively wide variations in and high intensity of SEMG activity. A first period of illumination at points 22 & 24 had little effect on SEMG activity. However, application of electromagnetic radiation (EMR) having a central wavelength of 520 nm (point 2) resulted in rapid, substantial decrease in SEMG activity. Further application of EMR at two locations, each involving a different central wavelength (point 3) further reduced the magnitude of variations and the relative SEMG activity.

In contrast with the substantial effects on the affected side, SEMG monitoring of the unaffected (right) side of this patient revealed comparatively little SEMG activity. Treatment of the affected side did not result in noticeable changes in SEMG activity on the non-affected side.

Patient 2

At the time of study, patient 2 was a 55 year old female having a history of left trapezius pain, congenital scoliosis and persistent limitations on range of motion. Years of physical therapy, chiropractic and allopathic intervention was without appreciable result. The subject was treated for three (3) sessions under IRB supervision using EMR in the visible spectrum (400 nm–700 nm). Application time was about 1 minute at each site. Five (5) combinations of central wavelength, and wavelength variation were used, each with continuous illumination (i.e., 100% duty cycle) according to Table 3 below.

TABLE 3

Treatment Protocol for Patient 2, First Session

| Treatment Time Index* | Treatment Locations** | Conditions of Illumination*** |
|---|---|---|
| 1 | 21 & 22 | 660 nm ± 60 nm |
| 2 | 6 & 14 | 420 nm |
| 3 | 19 & 20 | 700 nm ± 60 nm |
| 4 | 2 & 20 | 660 nm ± 60 nm |

TABLE 3-continued

Treatment Protocol for Patient 2, First Session

| Treatment Time Index* | Treatment Locations** | Conditions of Illumination*** |
|---|---|---|
| 5 | 6 & 14 | 600 nm |

*The number indicates that the illuminator was turned on. The + indicates that the illuminator was turned off.
**Locations shown in Table 1 above.
***Data expressed as central wavelength ± wavelength variation.

Figure 4A:
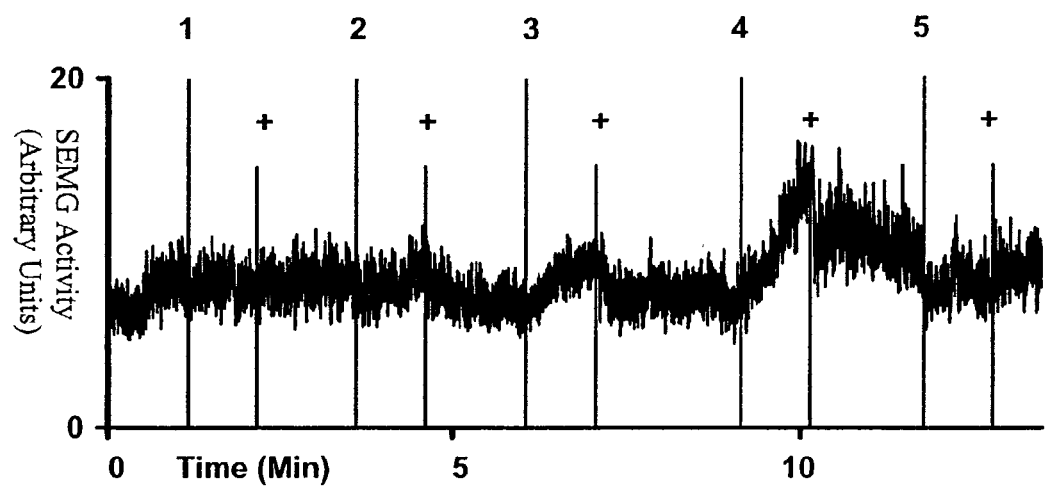
FIGS. 4a–4b depict SEMG traces of a subject different from that shown in FIGS. 3a and 3b having trapezius spasm.
Figure 4B:
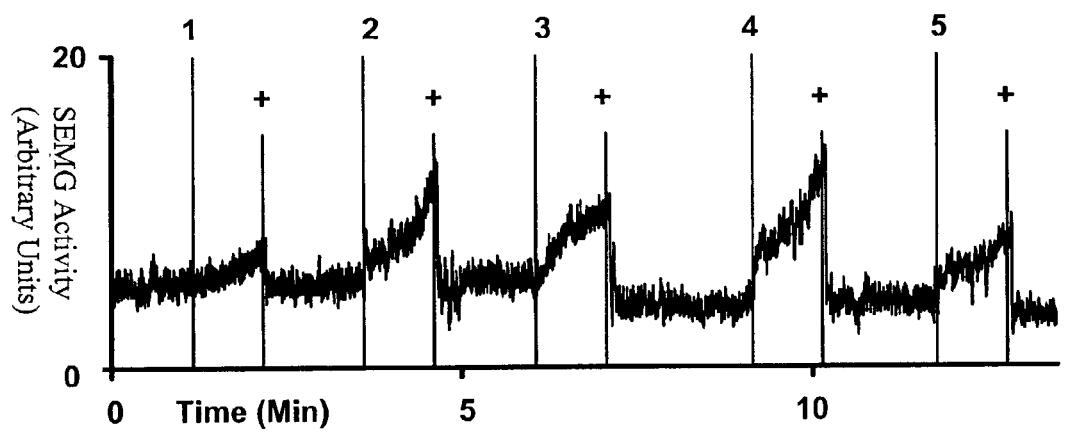

FIGS. 4a and 4b show the responses of patient 2 during a first therapy session. FIG. 4a shows the SEMG traces of the affected (left) side. Treatment at time indices 1 and 2 showed little change in the relatively variable activity. However, treatment at time index 3 resulted in a progressive alteration (increase) in SEMG activity, which returned to basal levels when the illuminator was turned off. Illumination at time index 4 (both sites on affected side) resulted in increased SEMG activity, which returned toward baseline values when the illuminator was turned off.

FIG. 4b shows the SEMG traces of the unaffected (right) side. Illumination at each time period resulted in progressive, increasing SEMG activity, which returned toward baseline values when the illuminator was turned off.

After the course of therapy, the patient reported that her muscles felt softer and that her range of motion improved, so that she could swim and move about more easily.

Patient 3

Patient 3 at the time of study, was a 53 year old female who received injuries as a passenger in an automobile when a piece of concrete fell from a bridge, through the front window and struck her. The object struck the patient in the head rendering her unconscious. She experienced persistent pain and muscle tightness on the right side. She had multiple courses of conventional treatments which did not result in alleviation of her muscular distress.

The subject was treated for three (3) sessions under IRB supervision using EMR in the visible spectrum (400 nm–700 nm). Application time at each site treated was approximately one minute. Six (6) sites identified in Table 1 above were illuminated according to Table 4 below.

TABLE 4

Treatment Protocol for Patient 3

| Treatment Time Index* | Treatment Locations** | Conditions of Illumination*** |
|---|---|---|
| 1 | 8 & 16 | 520 nm ± 40 nm |
| 2 | 6 & 14 | 520 nm ± 40 nm |
| 3 | 22 & 24 | First end effector: 620 nm ± 20 nm<br>Second end effector: 420 nm ± 20 nm |
| 4 | 2 & 20 | First end effector: 660 nm ± 40 nm<br>Second end effector: 420 nm ± 40 nm |
| 5 | 3 & 4 | 660 nm ± 40 nm |
| 6 | 6 | First end effector: 560 nm ± 20 nm<br>Second end effector: 420 nm ± 20 nm |

*The number indicates that the illuminator was turned on. The + indicates that the illuminator was turned off.
**Locations shown in Table 1 above.
***Data expressed as central wavelength ± wavelength variation. Illumination was constant during the time indices.

Figure 5A:
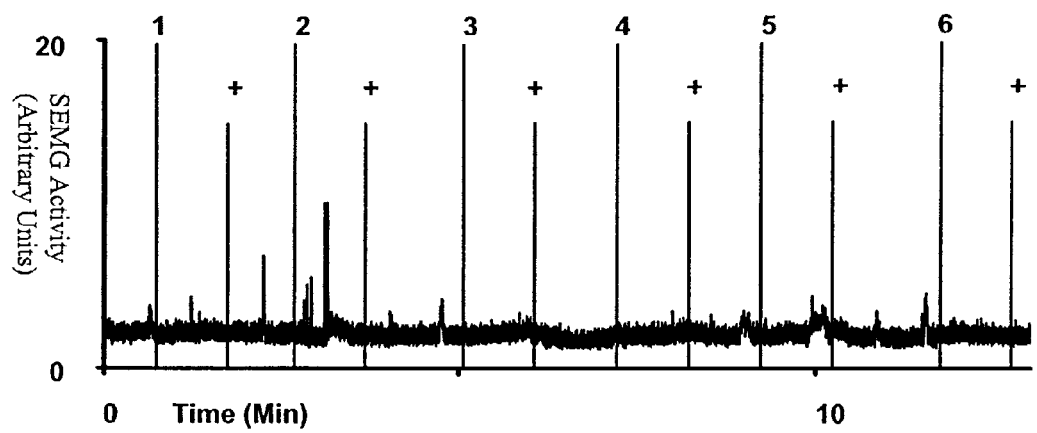
FIGS. 5a–5b depict SEMG traces of a another subject having trapezius spasm.
Figure 5B:
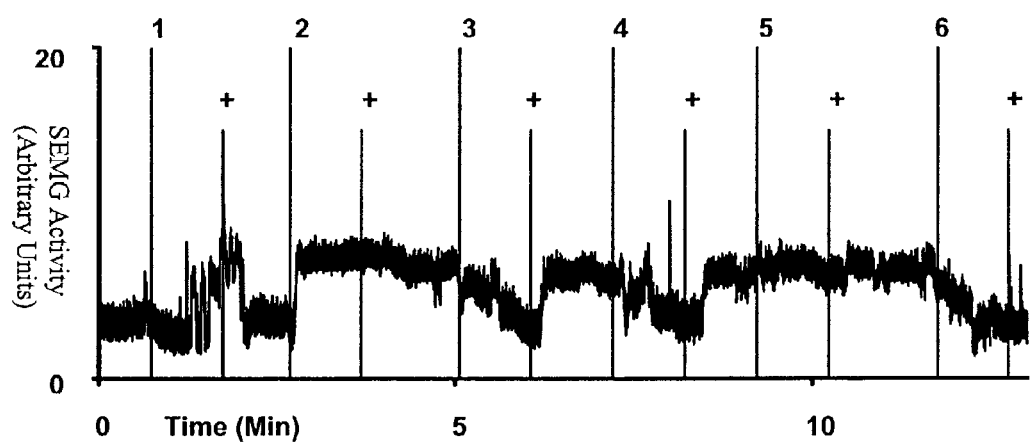

FIGS. 5a and 5b depict SEMG responses of patient 3 during the first of the three sessions. FIG. 5a shows the SEMG trace of the unaffected side (left side). The SEMG trace remained at a relatively constant, and low magnitude for the duration of the study, regardless of the location of or existence of illumination. FIG. 5b depicts the SEMG trace obtained from the affected side (right side) of patient 3. Before illumination, the variation in the SEMG trace was substantially greater than that of the unaffected side. During the first illumination period (time index 1), there was a lag period, followed by a slow rise in SEMG activity, which ended upon turning off the illuminator (+). A second period of illumination (time index 2) resulted in an increase in activity that persisted even after the illumination was terminated. At time index 3, the magnitude of SEMG activity decreased, and this decrease was reversed by terminating the exposure (+). Subsequently, at time index 4, SEMG activity decreased, and the decrease was reversed upon termination of exposure. At time index 6, activity decreased back to the pre-illumination base line value.

After the course of therapy, the patient reported increased mobility, softer muscles, and a 20% reduction in symptoms.

Patient 4

At the time of study, patient 4 was a 65 year old male experiencing insidious spasm of the right trapezius muscle which had been a problem for the prior 20 years, with persistent right sided pain and muscle tension and sleeplessness. No prior course of allopathic therapy was effective.

Patient 4 was treated for three (3) sessions, according to the protocol shown in Table 5 below.

TABLE 5

Treatment Protocol for Patient 4

| Treatment Time Index* | Treatment Locations** | Conditions of Illumination*** |
|---|---|---|
| 1 | 5 & 6 | 660 nm ± 60 nm |
| 2 | 13 & 14 | 540 nm |
| 3 | none | |
| 4 | 1 & 2 | 600 nm |

*The number indicates that the illuminator was turned on. The + indicates that the illuminator was turned off.
**Locations shown in Table 1 above.
***Data expressed as central wavelength ± wavelength variation. Illumination was constant during the time indices.

Figure 6A:
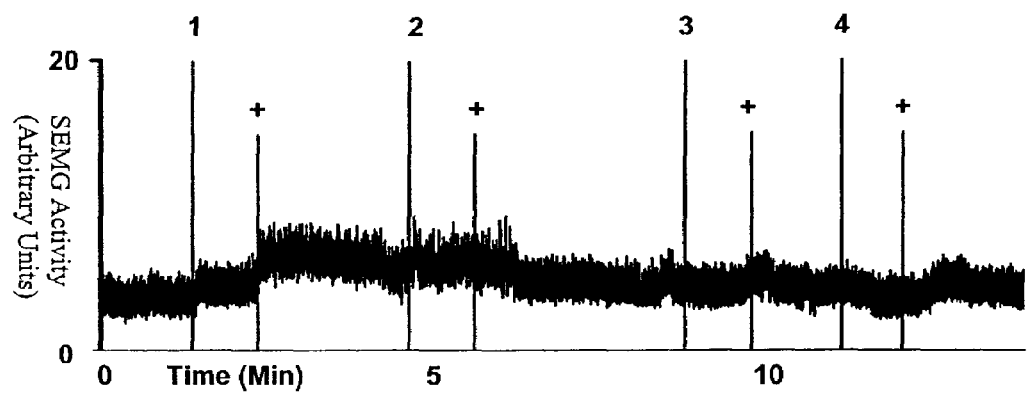
FIGS. 6a–6b depict SEMG traces of another subject having trapezius spasm.
Figure 6B:
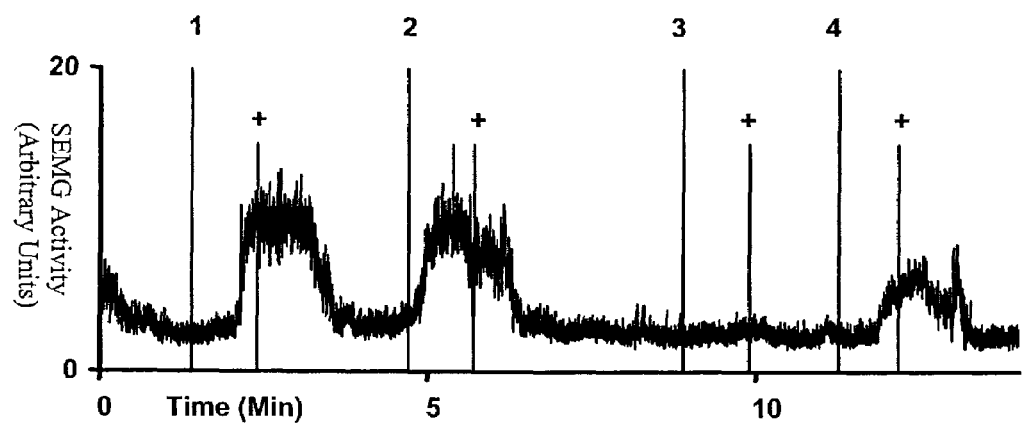

FIGS. 6a and 6b depict SEMG traces from patient 4. FIG. 6a depicts the SEMG trace obtained from the unaffected (left) side, and shows relatively low levels of activity. Application of EMR at time index 1 resulted in a slight increase in SEMG activity, and termination of the exposure resulted in a further, but small increase in activity. No other significant changes in SEMG activity were observed.

In contrast to the unaffected side shown in FIG. 6a, FIG. 6b shows the SEMG trace obtained from the affected side. Prior to illumination, baseline SEMG activity was decreasing. At time index 1, after a lag period, SEMG activity increased substantially. The increased activity persisted for a period after the illuminator was turned off (+), but then decreased to baseline values. Application of EMR at time index 2 resulted in a similar increase in SEMG activity. At time index 3, where the light beam was not directed at the patient, resulted in no change in SEMG activity. Illumination at time index 4 resulted in a lag period followed by an increase in SEMG activity, that reversed after the illuminator was turned off (+). We note that the magnitude of the increase in SEMG activity decreased progressively with time, indicating that the SEMG activity of the two sides became more alike with treatment.

After the course of three sessions, the patient reported lessening of muscle spasm and at least a 50% reduction in pain. He also reported normal sleep patterns.

The results of the studies of these 4 patients indicates that illumination of specific points on a patient's body, on the skin, can affect neuromuscular activity. Further, a program of therapy can be targeted to changing the muscular activity to relatively balanced levels, which can be associated with improved clinical signs and symptoms.

EXAMPLE 6

Treatment of Carpal Tunnel Syndrome I

Subjects suffering from carpal tunnel syndrome (CTS) were identified based on clinical findings and the subjects' reports. Seven (7) subjects were studied according in an IRB supervised study.

The purposes of the study were to determine whether application of EMR to selected locations on the hand, wrist, and/or arm produce therapeutic relief in patients with chronic pain due to carpal tunnel syndrome.

Somatosensory testing, nerve conduction velocity, high resolution thermal imaging and monofilament testing were performed before treatment was started. The same tests were made for comparison at other times during the study. Monofilament testing was performed at each session before treatment.

The initial treatment location for the subjects was the median nerve at the wrist. The initial central wavelength was 560 nm at a frequency of 20 Hertz.

Patient 1

Patient 1 at the time of study was a 44 year old female employed in the food service industry. Prior to treatment, she had problem with her right wrist for 16 years and was diagnosed by her orthopedist 8 years ago as suffering from CTS. She attributes the problem to playing athletics (softball pitcher and bowling). The pain was not localized and it travels from the wrist up the entire arm. She described it as very severe (#8 out of 10) with the character of sharp and shooting pain, associated with loss of function and inability to use her arm and hand. The pain was intermittent and was made worse by using her hand.

Before treatment, her grip strength was determined to be at the 76th percentile for women of her age. Her distal motor latency was 4.1 milliseconds (ms) (0.8 percentile).

After two treatments she reported that she went back to work and experienced no problem with her hand. She reported that her grip was very much improved and that she had good use of her hand. After the third treatment, she reported that the tingling and numbness were gone. Although she reported that some soreness around her wrist persisted, but that she could hold onto her coffee cup and that there was less pain on the side of her arm.

After three treatments, her grip strength improved to the 93d percentile, her distal motor latency decreased to 3.7 ms (8.4 percentile for age matched control women).

Patient 2

At the time of study, patient 2 was a 53 year old female hairdresser and cook. She complained of constant throbbing pain in her right hand that traveled up her arm to the shoulder. The throbbing has been present for more than ten years. The symptoms were made worse by constant hand movements as a hair dresser and lifting heavy pots and scrubbing them. She obtained some relief by not using her hand and soaking her hand in hot water. Her pain was graded as severe (grade 5). She first received sham treatment for two sessions. She reported no change in her symptoms. She then received an active treatment with central wavelength variation and reported that she was able to do hair all day long and experienced no numbness or tingling, but some aching persisted.

Patient 3

At the time of study, patient 3 as a 78 year old male working 10 hours/week in hardware store. He complained of pain in his right hand for many years but two years ago numbness slowly began to increase and was getting worse up to the time of study. The disorder was confirmed by monofilament testing and temperature threshold measurements as shown in Table 6 below.

TABLE 6

| | Patient 3 | | | | |
|---|---|---|---|---|---|
| | Thumb Cold Threshold* | Thumb Warm Threshold** | Thumb Vibration Threshold | Thumb Monofilament Threshold | Wrist Monofilament Threshold |
| Before Treatment | 14.0 | 48.6 | 16.9 μm | >11.5 gms insensitive | >11.5 gms insensitive |
| After 3 Treatments | 22.4 | 43.4 | 4.3 μm | <0.5 mg normal | <0.5 gm normal |

*, **Data expressed as degrees C.

Before treatment, he could not button his shirt nor was he able to pull up his zipper well. He had problems feeling coins in order to give proper change while working in the store. He experienced numbness which was constant and worse in his fingertips.

After one active treatment session he reported the following day that he felt improved sensation and the numbness decreased. He was able to make change better than before and he was able to feel the tab on his zipper in order to pull it up. After the second treatment session he reported that he felt great, the hand was more comfortable and the tingling was gone. He is not awakened by his hand during the night. He was able to squeeze the tip of his finger and feel it. He reported a dramatic improvement in his functional ability.

Patient 4

At the time of study, patient 4 was a 79 year old retired female, who reported using a cane in the right hand and began to notice tingling and numbness develop in the first three fingers of the right hand. She sought conventional treatment without relief. She was unable to type or to wring out a wash cloth. She felt somewhat improved by wearing a wrist brace while sleeping. She graded her pain as #8 (of 10) or very severe and was reported to be constant.

When she returned for her second treatment she reported that she did not have to wear a night brace at night and was able to sleep all night without pain. After her second treatment she reported that her symptoms became somewhat worse after playing cards all day but the spasms were not as severe as before.

Patient 5

At the time of study, patient 5 was a 49 year old female employed in sales. She was diagnosed as having CTS about 16 months prior to presenting. The onset was slow and gradual and the dull achy symptoms were made worse by driving and using a telephone. She reported chronic sleeplessness. If she shook her hand or bent it she did obtain some relief. The symptoms traveled from the fingers to her elbow. She reported that after her second treatment session that a lot of ache pressure is gone. There was no numbness or tingling. She reported that she was sleeping the night through.

Patient 6

At the time of study, patient 6 was a 41 year old female homemaker. She was involved in two severe automobile/train accidents in 1970 and 1994. She was gripping the steering wheel and was jerked severely at the time of accident. Her symptoms were made worse by attempting to operate a vacuum, washing windows, using a computer or holding the telephone. She was able to obtain some relief by using a wrist band at night. Sometimes the pain traveled up her arm but it concentrated in her thumb. It was intermittent.

After two treatments, she reported that she felt some improvement with a decrease in stiffness in her hands.

Patient 7

At the time of study, patient 7 was a 66 year old female cook. Ten years ago she was scrubbing pots and pans in a circular motion while performing her occupational duties and developed left handed pain. She operated a French fryer for 1.5 hours which required her to continually lift and empty the frying basket. This caused her to experience additional pain. Lifting and grasping made her symptoms worse and using a wrist brace at night help relieve the pain. The symptoms did not travel or move and they were constant while she was at work. Prior to treatment, her grip strength was reported to be in the 46th percentile for her age. Her distal motor latency was 4.1 ms and the percentile based on age was 0.4%.

After three treatments, her grip strength improved to the 54th percentile, her distal motor latency decreased to 3.7 ms (7.8 percentile). After her first treatment session she reported that she was able to sleep without her brace and her hand did not get numb. After the second treatment session she reported that her hand did not go to sleep and there was no numbness or tingling. She has not been awakened from sleep.

These studies indicate that under control conditions in which no EMR was delivered, the subjects reported no changes in either symptoms, objective evaluation of physiological variables or in clinical findings. However, treating the subjects with the electromagnetic radiation improved function, decreased symptoms of pain and improved objective measurements of physiological variables. No adverse effects of EMR therapy were reported.

EXAMPLE 8

Treatment of Carpal Tunnel Syndrome II

In a larger study of patients with carpal tunnel syndrome (CTS), sixteen (16) patients are evaluated under IRB supervision. The subject population is divided into two equal groups of eight (8) subjects before start of the study. One group receives treatment with the electromagnetic radiation turned "on" for each of the first two treatments. The other group receives treatment with the electromagnetic radiation turned "off" for the first two treatments. The first group receives two treatments with the electromagnetic radiation turned "off" at later times in the study. All subjects receive a maximum of eight (8) treatments with the electromagnetic radiation turned "on" during the course of one month.

The initial treatment location for the subjects is the median nerve at the wrist. The initial central wavelength is 560 nm at a frequency of 20 Hertz. Additional subjects initial treatment includes a wavelength variation of ±20 nm during treatment.

We observe that EMR therapy results in improved mobility, decreased pain, increased ability to move.

IV Methods of Monitoring Electromagnetic Radiation Therapy

Many methods are known in the art to be beneficial for assessing the efficacy of treatment. The monitoring system chosen can be advantageously selected based on the diagnosis, the affected tissue or organ, and on the type of treatment used. Methods include, but are not limited to the following.

Photoplethysmography ("PPG") is a method for noninvasively monitoring blood volume changes in an extremity such as a finger, toe, or in alternative embodiments, a hand, foot, arm or leg. Plethysmography can be used to track cardiac pulse rate, heart rate variability, changes in pulse pressure and peripheral blood flow.

Surface electromyography ("sEMG" or "SEMG") involves the use of two or more electrodes placed over a muscle. Muscular activity is reflected in changes in electrical activity of the muscle, and changes in electrical activity can reflect the underlying tone or activity of the muscle. SEMG can be used to identify points on a patient's body that are responsive to electromagnetic radiation therapy. EMT can be applied to various points on the body, and an alteration in SEMG activity can indicate that the point so treated is associated with activity of the muscle monitored by SEMG.

Temperature monitoring can be carried out using liquid crystal temperature scales attached to the skin, temperature sensors taped to the skin temperature probes touched to the skin or electronic thermography using infrared cameras.

Respiration monitoring using sensitive force transducers can be used to monitor respiration rate and alterations in rate, depth and pattern of breathing.

Doppler blood flow measurements can be made using equipment that delivers sound waves or laser light to tissues that are moving. Because blood flow involves linear motion of blood, the velocity with which blood moves can be accurately measured.

Electrodermal activity ("EDA") can be monitored using skin conductance response ("SCR") and skin conductance level ("SCL") can be used to monitor changes in sympathetic nerve activity to sweat glands in the skin. Sensors can be attached to different points on the patient's skin and the conductivity between those sensors can be displayed in real time.

Tissue compliance measurements ("TCL") can be used using standard gauges to quantify alteration in muscle spasticity, muscle tension, tone, edema, scarring, presence of fibrotic tissue, and changes in stump density before and after treatment.

Pressure threshold measurement can be used to quantify the minimum amount of pressure that can be detected in painful regions associated with fibromyalgia, myofascial syndrome, myositis, nerve irritation, and certain endocrine and metabolic conditions.

Pressure tolerance measurements can be used to quantify the maximum amount of pressure that can be tolerated.

Current perception threshold devices can be used to determine sensory nerve conduction threshold ("sNCT") evaluations by determining the amount of current that can pass without causing pain ("CPT"). CPT and sNCT can be used to quantify conduction and functional integrity of large and small myelinated and unmyelinated sensory nerve fibers at cutaneous sites. This information can be used to detect and quantify early stage neuritis and peripheral sensory neuropathies. Constant current output assures highly reproducible measures, which are unaffected by variables such as skin thickness, temperature or edema.

Pulse oximetry can be used to document changes in pulse rate, peripheral oxygen content and saturation, and can be used to detect changes in peripheral perfusion.

Alizarin sweat test is a noninvasive procedure to assess activation of the sweat glands as a result of sympathetic nervous system activity.

Monofilament testing can be used at hyperesthetic or hypoesthethic regions to quantify changes in sensory function. Regions can be mapped, recorded and kept in a patient's record.

Dual-inclinometry measurements can be taken of joints that are functionally impaired with pain as a limiting factor. Those joints which are restricted and not part of the patient's primary complaint can be measured if desired. Measurements can be serially repeated to chart functional improvement.

Jamar grip and pinch strength measurements can be repeated three times at each of five settings and then can be graphed. The average pinch and grip strengths can then be compared to age and sex-matched normative data to determined sincerity of effort in performance of testing and as a monitoring methods to document strength augmentation with therapy.

Gait analysis can be performed using video recording equipment. The patient can use usual and customary ambulatory aids and walks toward and away from the camera for at least five steps. The legs can be exposed from the knees downward and the customary foot wear is worn. The practitioner may elect to record an analysis while the patient wears either no footwear, or while wearing orthotics or other prescriptive aids.

Limited functional capacity evaluation can be conducted on an individual and regional basis exclusively for the symptomatic region. Photography, including digital photography can be used to record asymmetry of movement, posture, (sitting and standing) and any region that is included in the patient's primary complaint region. Comparative evaluations can be conduced in a serial manner to monitor improvement in posture.

Muscle strength testing can be conducted with standard hand-held resistance gauges to quantify lift to right asymmetries and to monitor functional improvement. Muscles to be tested can be within the patient's primary pain or dysfunction area. Measurements can be repeated to provide reliable information.

Somatosensory evoked potentials can be performed to quantify neural integrity status and/or improvement following a course of treatment. Typically, temperature and/or vibratory stimuli are provided and the sensitivity of the subject to these stimuli can be quantified. In certain cases, it can be desirable to monitor asymmetry of responses. Initial examinations can assist the practitioner in the placement of sites for treatment and subsequent evaluations can quantify progress and determine maximum therapeutic benefit.

Motor and sensory nerve conduction velocity studies ("CVS") can be performed as an initial evaluative technique. Nerves to be treated can be selected on the basis of conduction velocity in certain embodiments of this invention. Working diagnosis can be provided and CVS can be used to make comparative evaluations.

Electrodermal testing can be conducted prior to treatment and can be designed to address symptomatic regions in lieu of testing for general well-being. The test can be repeated serially to quantify effectiveness of current treatment regimens and as an aid in evaluating an individual patient's responses. Electrodermal testing can also be used to determine effectiveness of treatment with radiation of specific wavelengths and wavelength ranges.

Dermathermagraph readings can be performed for patients whose problems are spinal in nature, can be recorded and stored in a patient's chart.

Electroencephalograms can be performed when head trauma, closed head injury, cognitive dysfunction or prior testing abnormalities were noted. Comparative evaluations can be conducted to objectify improvement and to maintain goal orientation.

Neurobiofeedback evaluations can be conduced for central nervous system abnormalities.

TerraHertz wave ("T-wave") imaging can be used to visualize soft tissues, and may be especially useful for diagnosing disorders of connective tissues.

Digital photography can be conducted in cases of skin lesions including vascular insufficiency or other clearly observable conditions. A linear, standardized color scale can be placed on the skin, to quantify the region of observation. Date and time information can be recorded and comparative evaluations can be conducted serially and recorded for future comparisons. In situations in which electromagnetic radiation therapy is being used, frequent images can be recorded to provide easy comparisons during the course of therapy.

Postural evaluations can include scoliometers, pelvic asymmetry measurements, leg length measurements and the like can be used for patients whose therapeutic goals are directed at those sites.

Circumferential measurements can be performed on extremities in situations in which edema or swelling or atrophy is a component of the presenting symptoms and findings. Measurements can be taken at major joints and then more proximally or distally, or both. Measurements can also be taken on the contralateral side for baseline and'; or comparative reasons, and responses to treatment.

Broadband radar can be used to monitor rigidity of internal muscles, such as deep muscles of the leg.

Computers can be advantageously used to store, recall and compare information on a patient's progress. For example, computerized algorimetry can establish a patient's response to compression on the symptomatic as well as asymptomatic sides for conditions that present laterally on the body. Stored data can be recalled and compared with currently obtained data. Histograms comparing variables can be produced to make comparisons easy. Computerized monofilament testing can be used to quantify sensory perception threshold to light touch of a patient.

Skin pH measurements can be made, and can reflect normalization of function of cellular function.

The above methods and devices are included by way of example only. Other types of measurements can be advantageously used with the methods of this invention to improve diagnosis and to follow the progress of treatment.

The foregoing descriptions are provided by way of example only. Other similar methods can be used to treat other conditions having related physiological characteristics. Workers of ordinary skill in the art can readily appreciate that variations of the methods described herein are considered to be part of this invention.

INDUSTRIAL APPLICABILITY

This invention provides methods for treating a variety of disorders using electromagnetic radiation directed at excitable tissues, including nerves, muscles and blood vessels. The electromagnetic radiation therapy can be used in conjunction with other forms of symptomatic therapy, including allopathic remedies, chiropractic and other forms of treatment known in the medical and health care arts.

We claim:

1. A method for treating headache in a subject, comprising the steps of:
   (a) exposing a portion of the occipital nerve with a beam of electromagnetic radiation having a wavelength in the range of about 597 nm to about 622 nm, and having a controlled variable selected from the group consisting of:
      (i) wavelength;
      (ii) bandwidth;
      (iii) pulse duration;
      (iv) pulse frequency;
      (v) intensity; and
      (vi) wavelength variation over time; and
   (b) monitoring a response of a tissue associated with said headache.

2. The method of claim 1, wherein said step of exposing includes exposing said portion of the occipital nerve to a beam of electromagnetic radiation at an angle of about 45° to the cephalad.

3. The method of claim 1, further comprising stimulating said subject with a beam of electromagnetic radiation at a site near the inner canthus of the eye, said radiation having a controlled variable selected from the group consisting of:
   (i) wavelength;
   (ii) bandwidth;
   (iii) pulse duration
   (iv) pulse frequency;
   (v) intensity; and
   (vi) wavelength variation over time.

4. The method of claim 1, wherein the wavelength of radiation is in the range of about 577 nm to about 597 nm.

5. The method of claim 1, wherein the wavelength of radiation is in the range of about 577 nm to about 622 nm.

6. A method for treating neuronal pain in a subject, comprising the steps of:
   (a) exposing an affected tissue associated with said nerve to electromagnetic radiation having a wavelength in the range of about 400 to about 700 nm, and a controlled variable selected from the group consisting of:
      (i) wavelength;
      (ii) bandwidth;
      (iii) pulse duration;
      (iv) pulse frequency;
      (v) intensity; and
      (vi) wavelength variation over time; and
   (b) monitoring a response of said affected tissue.

7. The method of claim 6, further comprising the step of exposing a contralateral nerve associated with said pain.

8. The method of claim 6, further comprising the step of exposing said subject to radiation at a site proximal to the site in step (a).

9. The method of claim 6, wherein said pain is associated with a disorder selected from the group consisting of complex regional pain syndrome, sympathetic dystonia, reflex sympathetic dystrophy, post surgical pain, muscle spasm, carpal tunnel syndrome, peripheral neuropathy, tarsal tunnel syndrome, dental pain, gingivitis, and traumatic injury.

10. A method for treating neuronal pain in a subject, comprising the steps of:
    (a) exposing a site near C1 to electromagnetic radiation in the visible wavelength range having a controlled variable selected from the group consisting of:
       (i) wavelength;
       (ii) bandwidth;
       (iii) pulse duration;
       (iv) pulse frequency;
       (v) intensity; and
       (vi) wavelength variation over time; and
    (b) monitoring a response of a tissue associated with said neuronal pain.

11. A method for treating sympathetic hyperactivity in a subject, comprising the steps of:
    (a) exposing a blood vessel associated with said sympathetic hyperactivity to electromagnetic radiation in the visible wavelength range having a controlled variable selected from the group consisting of:
       (i) wavelength;
       (ii) bandwidth;
       (iii) pulse duration;
       (iv) pulse frequency;
       (v) intensity; and
       (vi) wavelength variation over time; and
    (b) monitoring a response of a tissue associated with said blood vessel.

12. The method of claim 11, wherein said blood vessel is selected from the group consisting of the abdominal aorta, the femoral artery, the brachial artery and the popliteal artery.

13. A method for treating temporomandibular joint syndrome in a subject, comprising the steps of:
    (a) exposing a tissue associated with said temporomandibular joint syndrome to electromagnetic radiation in the visible wavelength range having a controlled variable selected from the group consisting of:
       (i) wavelength;
       (ii) bandwidth;
       (iii) pulse duration;
       (iv) pulse frequency;
       (v) intensity; and
       (vi) wavelength variation over time; and
    (b) monitoring a response of a tissue associated with said syndrome.

14. The method of claim 13, wherein said wavelength is in the range of about 577 nm to about 622 nm.

15. The method of claim 13, additionally comprising the step of subsequently exposing said tissue to electromagnetic radiation having a wavelength in the range of about 455 nm to about 492 nm.

16. A method for treating trigeminal neuralgia, comprising the steps of:
    (a) exposing a tissue associated with trigeminal neuralgia to electromagnetic radiation in the visible wavelength range having a controlled variable selected from the (i) wavelength;
(ii) bandwidth;
(iii) pulse duration;
(iv) pulse frequency;
(v) intensity; and
(vi) wavelength variation over time; and
(b) monitoring a response of a tissue associated with trigeminal neuralgia.

17. A method for treating a abnormalities of vascular perfusion, comprising the steps of:
(a) exposing a portion of a tissue associated with said abnormality of vascular perfusion to an effective amount of electromagnetic radiation having a controlled wavelength in the visible wavelength range; and
(b) monitoring a change in a characteristic of said tissue associated with said radiation.

18. The method of claim 17, wherein said abnormality of vascular perfusion is associated with a disorder selected from the group consisting of complex regional pain syndrome, sympathetic dystonia, reflex sympathetic dystrophy.

19. A method for treating a subject having a neuromuscular abnormality, comprising the steps of:
(a) identifying a site of a neuromuscular abnormality;
(b) selecting at least one site on said subject's body for electromagnetic radiation therapy (ERT); and
(c) exposing said at least one site for ERT to a beam comprising an effective amount of electromagnetic radiation having a wavelength in the visible range.

20. The method of claim 19, wherein said wavelength of electromagnetic radiation comprises a central wavelength and said wherein wavelength changes with time by a predetermined wavelength variation around said central wavelength.

21. The method of claim 20, wherein said wavelength variation is in the range of about 1 nm to about 100 nm.

22. The method of claim 20, wherein said wavelength variation occurs with a cycle time in the range of about 1 sec to about 100 sec.

23. The method of claim 20, wherein said wavelength variation occurs in a linear fashion.

24. The method of claim 20, wherein said wavelength variation occurs in a pattern selected from the group consisting of v-waves, sine waves and trapezoidal waves.

25. The method of claim 19, wherein said neuromuscular abnormality is trapezius spasm.

26. The method of claim 19, wherein said neuromuscular abnormality is carpal tunnel syndrome.

27. The method of claim 19, wherein said neuromuscular abnormality is lower extremity neuropathy.

28. The method of claim 19, wherein said neuromuscular abnormality is myofascial syndrome.

29. The method of claim 19, wherein said site selected in step (b) is an electrodiagnostic point, an acupuncture point, a trigger point, a meridian or is along a nerve distribution to said site of neuromuscular abnormality.

30. The method of claim 19, wherein said beam of electromagnetic radiation has a cross-sectional shape selected from the group consisting of circular, ellipsoidal, triangular and rectangular.

31. The method of claim 19, wherein said step (c) includes moving said beam of electromagnetic radiation between locations selected in step (b).

32. The method of claim 19, wherein two sites are selected in step (b) and a first beam of electromagnetic radiation is directed to a first site and wherein a second beam of electromagnetic radiation is directed at a second site.

33. The method of claim 32, wherein said fist beam has at least one property selected from the group consisting of central wavelength, wavelength variation, frequency, change in frequency, intensity, change in intensity or duration of application that is different from the corresponding property of said second beam.

* * * * *

UNITED STATES PATENT AND TRADEMARK OFFICE
CERTIFICATE OF CORRECTION

PATENT NO. : 7,150,710 B2
APPLICATION NO. : 10/180802
DATED : December 19, 2006
INVENTOR(S) : Constance Haber et al.

It is certified that error appears in the above-identified patent and that said Letters Patent is hereby corrected as shown below:

Col. 2, line 3: after "skin" and before "taken" delete "is" and insert --and--.
Col. 2, line 6: after "cells" and before "produce" insert --to--.
Col. 2, line 60: after "with" and before ". Additionally" delete "case" and insert --ease--.
Col. 8, line 7: after "The" and before "wavelengths" insert --group of--.
Col. 9, line 8: after "groups" and before "wavelengths" insert --of--.
Col. 9, line 42: after "other" and before "wavelengths" delete ",".
Col. 9, line 63: after "receptors." and before "the" delete "By selecting" and insert --Selecting--.
Col. 10, line 60: after "be" and before "near" delete "place" and insert --placed--.
Col. 12, line 23: after "area" and before "constructed" delete "maybe" and insert --may be--.
Col. 13, line 26: after "mechanism" and before "placed" delete "maybe" and insert --may be--.
Col. 14, line 27: before "series" delete "In one" and insert --One--.
Col. 14, line 53: after "reflector" and before "used" delete "maybe" and insert --may be--.
Col. 17, line 32: after "lengths" and before "absorbed" delete "maybe" and insert --may be--.
Col. 17, line 41: after "radiation" and before "manifested" delete "maybe" and insert --may be--.
Col. 25, line 19: after "invention" and before "treating" delete "involves" and insert --involve--.
Col. 42, Table 6, under the Column "Thumb Monofilament Threshold" delete "mg" and insert --gm--.

Signed and Sealed this

Fourth Day of December, 2007

JON W. DUDAS
*Director of the United States Patent and Trademark Office*